United States Patent
Orlov et al.

(10) Patent No.: US 8,758,431 B2
(45) Date of Patent: Jun. 24, 2014

(54) CARDIAC VALVE LEAFLET AUGMENTATION

(75) Inventors: Boris Orlov, Haifa (IL); Nisan Zef, Kiryat-Yam (IL)

(73) Assignee: Mor Research Applications Ltd., Tel-Aviv (IL)

(*) Notice: Subject to any disclaimer, the term of this patent is extended or adjusted under 35 U.S.C. 154(b) by 393 days.

(21) Appl. No.: 12/602,807

(22) PCT Filed: Jun. 4, 2008

(86) PCT No.: PCT/IL2008/000758
§ 371 (c)(1),
(2), (4) Date: Dec. 3, 2009

(87) PCT Pub. No.: WO2008/149355
PCT Pub. Date: Dec. 11, 2008

(65) Prior Publication Data
US 2010/0204662 A1    Aug. 12, 2010

Related U.S. Application Data

(60) Provisional application No. 60/924,869, filed on Jun. 4, 2007.

(51) Int. Cl.
*A61F 2/24* (2006.01)
(52) U.S. Cl.
CPC .............. *A61F 2/2463* (2013.01); *A61F 2/2466* (2013.01)
USPC ....................................................... 623/2.11
(58) Field of Classification Search
USPC ............. 623/2.11, 2.12, 2.17, 900, 904, 1.26, 623/2.38, 2.14; 606/167, 170, 185, 139, 606/142, 143, 151, 153–158, 213, 215, 184
See application file for complete search history.

(56) References Cited

U.S. PATENT DOCUMENTS

| | | |
|---|---|---|
| 5,725,552 A | 3/1998 | Kotula et al. |
| 5,846,261 A | 12/1998 | Kotula et al. |

(Continued)

FOREIGN PATENT DOCUMENTS

WO    WO 2008/149355    12/2008

OTHER PUBLICATIONS

International Search Report Dated Nov. 14, 2008 From the International Searching Authority Re.: Application No. PCT/IL2008/000758.

(Continued)

*Primary Examiner* — Ryan Severson
*Assistant Examiner* — Rachel S Papeika

(57) ABSTRACT

Methods and devices for augmenting an atrioventricular valve leaflet is disclosed. A method according to an exemplary embodiment includes piercing a leaflet of the valve to at least a portion of the leaflet's thickness to form a pierced section; and extending the leaflet using said pierced section. A device according to an exemplary embodiment of the invention includes a catheter comprising: a longitudinal tube having a lumen; and a cutting element extendable from the lumen. The cutting element is adapted for forming a limited cut in an atrioventricular valve. A device according to another exemplary embodiment of the invention includes a catheter comprising a longitudinal tube having a lumen; a cutting element extendable from the lumen and adapted for forming a cut in a leaflet of an atrioventricular valve; and a frame, configured to attach to the leaflet and stay attached to the leaflet when the heart beats.

22 Claims, 23 Drawing Sheets

(56) References Cited

U.S. PATENT DOCUMENTS

| | | | |
|---|---|---|---|
| 5,944,738 A | | 8/1999 | Amplatz et al. |
| 2004/0030382 A1 | | 2/2004 | St. Goar et al. |
| 2004/0092858 A1 | * | 5/2004 | Wilson et al. .................... 604/9 |
| 2004/0127981 A1 | * | 7/2004 | Rahdert et al. ............... 623/2.36 |
| 2004/0225300 A1 | | 11/2004 | Goldfarb et al. |
| 2006/0229659 A1 | * | 10/2006 | Gifford et al. ................ 606/200 |
| 2007/0118154 A1 | | 5/2007 | Crabtree |

OTHER PUBLICATIONS

Written Opinion Dated Nov. 14, 2008 From the International Searching Authority Re.: Application No. PCT/IL2008/000758.

Mack "Percutaneous Mitral Valve Repair: A Fertile Field of Innovative Treatment Strategies", Circulation, 113: 2269-2271, 2006.

International Preliminary Report on Patentability Dated Jan. 28, 2010 From the International Bureau of WIPO Re.: Application No. PCT/IL2008/000758.

* cited by examiner

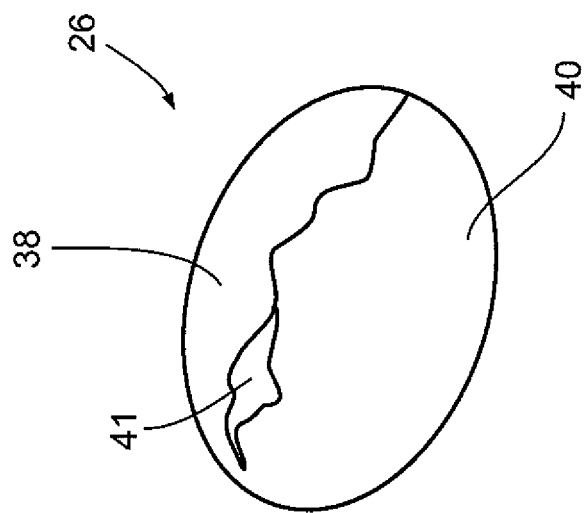
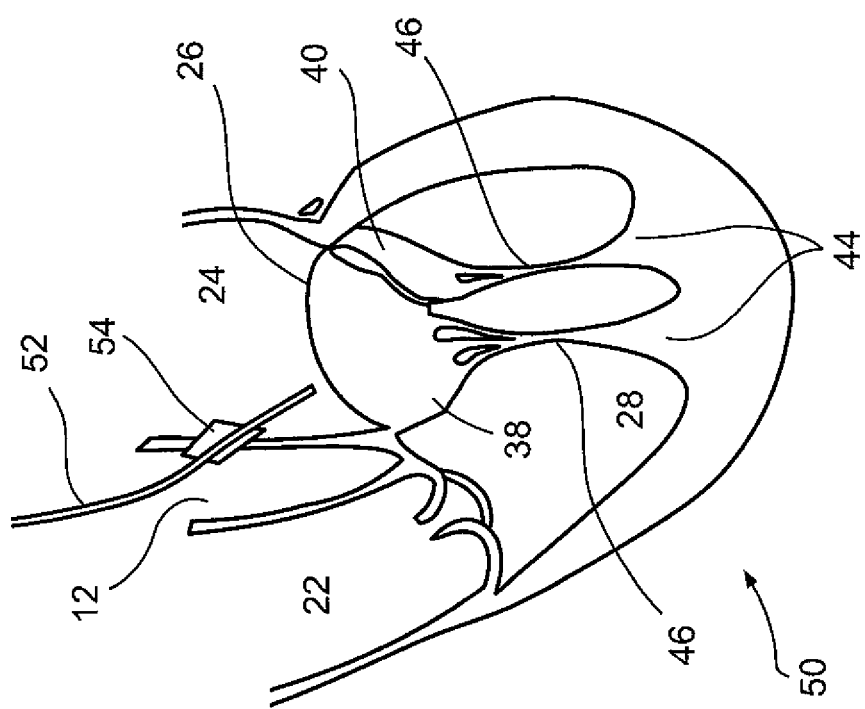
Fig. 4A
Fig. 4B

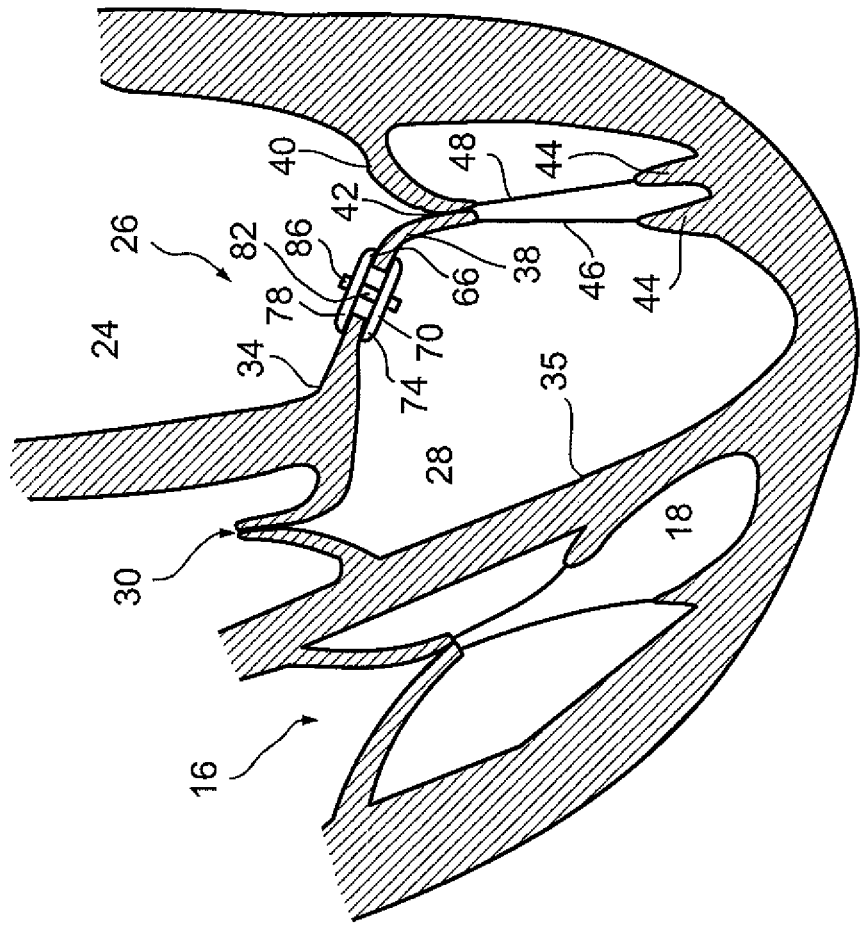
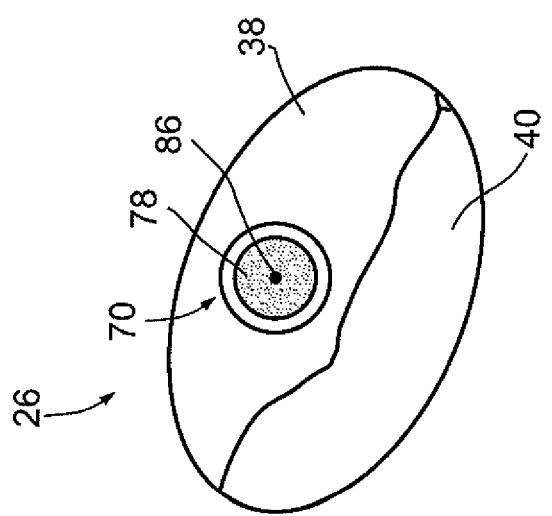
Fig. 4K
Fig. 4J

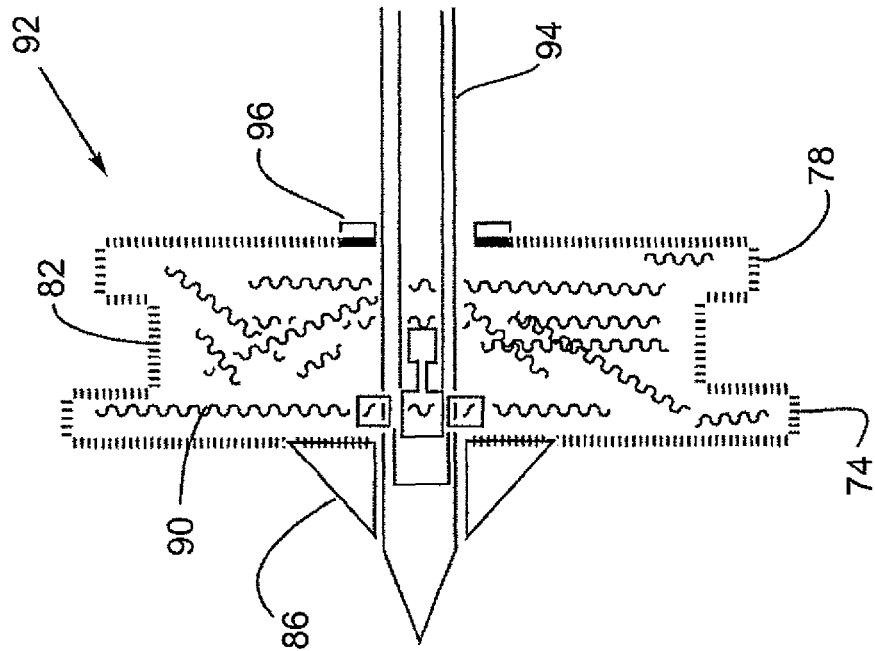
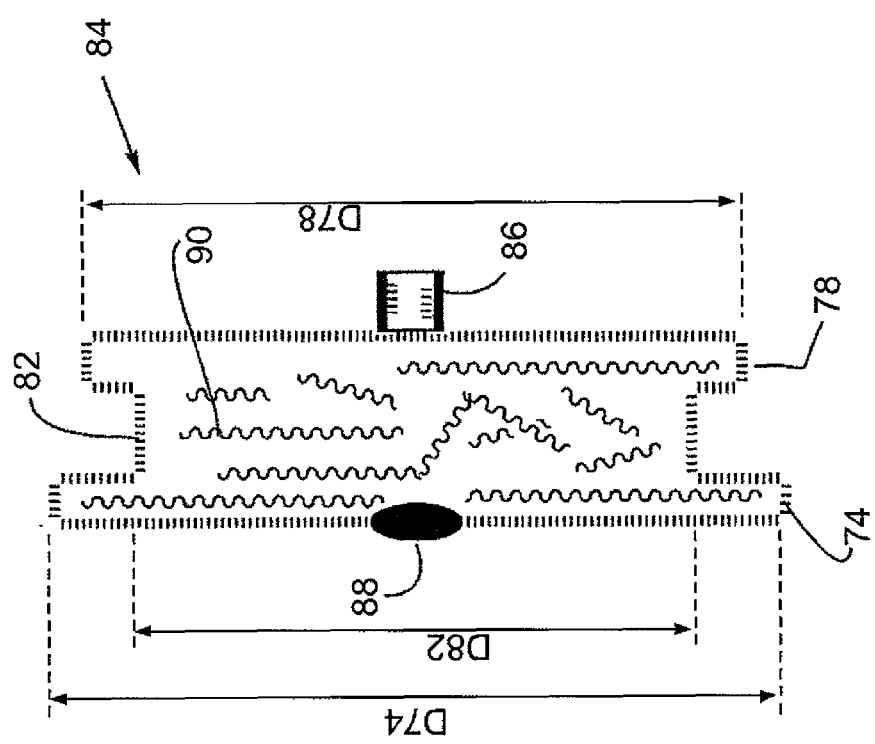
Fig. 5B
Fig. 5A

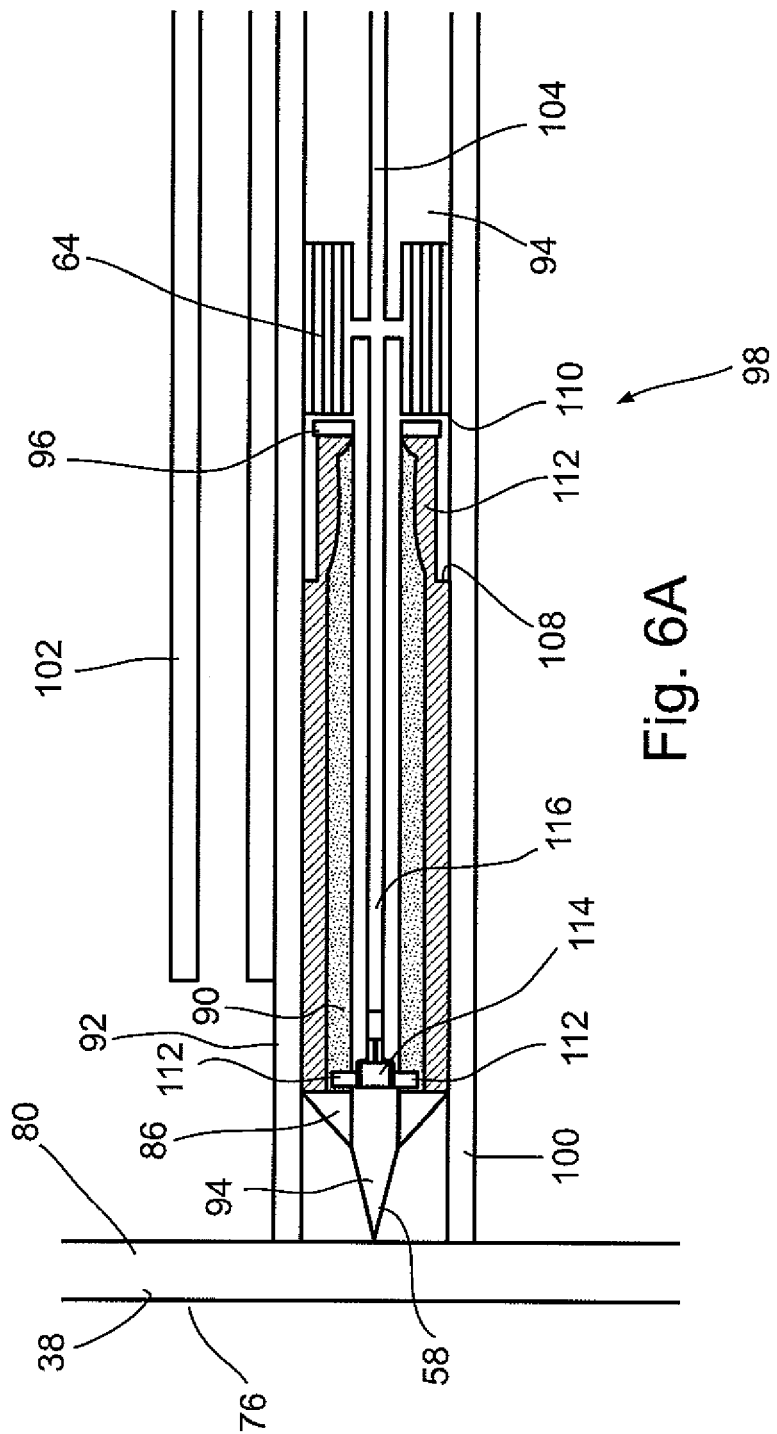

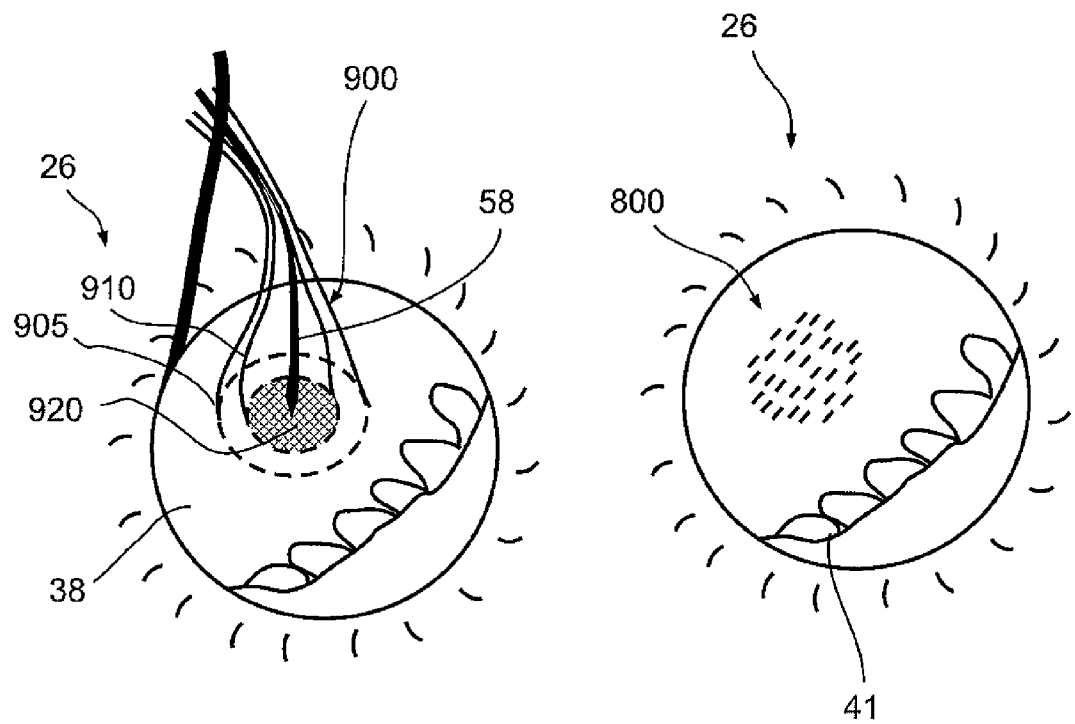
Fig. 9A
Fig. 8
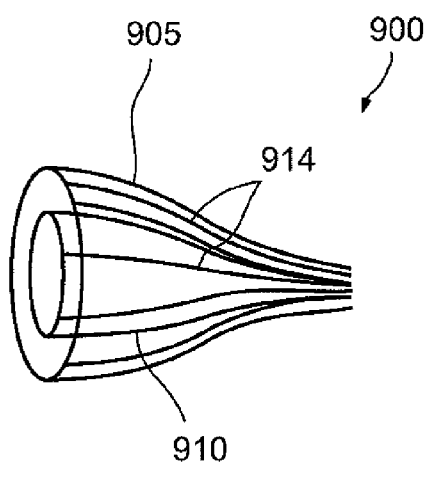
Fig. 9B
Fig. 9C

CARDIAC VALVE LEAFLET AUGMENTATION

RELATED APPLICATIONS

This Application is a National Phase of PCT Patent Application No. PCT/IL2008/000758 having International filing date of Jun. 4, 2008, which claims the benefit of U.S. Provisional Patent Application No. 60/924,869 filed on Jun. 4, 2007. The contents of the above Applications are all incorporated herein by reference.

FIELD AND BACKGROUND OF THE INVENTION

The present invention, in some embodiments thereof, relates to the field of cardiac medicine and more particularly but not exclusively to atrioventricular valve leaflet augmentation.

An aspect of some embodiments of the invention relates to improving the functioning of the mitral valve or the tricuspid valve. In the following, provided is a brief explanation of the structure of the mitral valve and its relation to the functioning of the heart in general. Afterwards, a brief explanation of mitral valve insufficiency and some treatments of this condition are described.

The Human Heart and the Mitral Valve

The human heart 10, depicted in cross sectional long axis view in FIG. 1, is a muscular organ that pumps deoxygenated blood through the lungs to oxygenate the blood and pumps oxygenated blood to the rest of the body by rhythmic contractions of four chambers.

After having circulated in the body, deoxygenated blood from the body enters the right atrium 12 through the vena cava 14. Right atrium 12 contracts, pumping the blood through a tricuspid valve 16 into the right ventricle 18. Right ventricle 18 contracts, pumping the blood through the pulmonary semi-lunar valve 20 into the pulmonary artery 22 which splits to two branches, one for each lung. The blood is oxygenated while passing through the lungs and reenters the heart to the left atrium 24.

Left atrium 24 contracts, pumping the oxygenated blood through the mitral valve 26 into the left ventricle 28. Left ventricle 28 contracts, pumping the oxygenated blood through the aortic semi-lunar valve 30 into the aorta 32. From aorta 32, the oxygenated blood is distributed to the rest of the body.

Physically separating left ventricle 28 and right ventricle 18 is interventricular septum 33. Physically separating left atrium 24 and right atrium 12 is an interatrial septum (25, FIG. 2b).

Mitral valve 26, depicted in FIG. 2A (top view) and in FIG. 2B (cross sectional long axis view) is defined by an approximately circular mitral annulus 34 that defines a mitral orifice 36. Attached to the periphery of mitral annulus 34 is an anterior leaflet 38 and a smaller posterior leaflet 40, leaflets 38 and 40 joined at commissures 41. Each leaflet is between about 0.8 and 2.4 mm thick and composed of three layers of soft tissue. The typical area of mitral orifice 36 in a healthy adult is between 4 and 6 cm² while the typical total surface area of leaflets 38 and 40 is approximately 12 cm². Consequently and as depicted in FIG. 2B, leaflets 38 and 40 curve downwards into left ventricle 28 and coapt to accommodate the excess leaflet surface area, producing a coaptation depthdepth 42 that constitutes a seal. The typical length of coaptation depthdepth 42 in a healthy heart 10 of an adult is approximately 7-8 mm.

The bottom surface of anterior leaflet 38 and posterior leaflet 40 are connected to papillary muscles 44 at the bottom of left ventricle 28 by posterior chordae 46 and anterior chordae 48.

During diastole, left atrium 24 contracts to pump blood downwards into left ventricle 28 through mitral valve 26. The blood flows through mitral orifice 36 pushing leaflets 38 and 40 downwards into left ventricle 28 with little resistance.

During systole left ventricle 28 contracts to pump blood upwards into aorta 32 through aortic semi-lunar valve 30. Mitral annulus 34 contracts pushing leaflets 38 and 40 inwards and downwards, reducing the area of mitral orifice 36 by about 20% to 30% and increasing the length of coaptation depthdepth 42. The pressure of blood in left ventricle 28 pushes against the bottom surfaces of leaflets 38 and 40, tightly pressing leaflets 38 and 40 together at coaptation depthdepth 42 so that a tight leak-proof seal is formed. To prevent prolapse of leaflets 38 and 40 upwards into left atrium 24, papillary muscles 44 contract pulling the edges of leaflets 38 and 40 downwards through posterior chordae 46 and anterior chordae 48, respectively.

Mitral Valve Insufficiency

As is clear from the description above, an effective seal of mitral valve 26 is dependent on a sufficient degree of coaptation, in terms of length, area and continuity of coaptation depth 42. If coaptation depth 42 is insufficient or non-existent, there is mitral valve insufficiency, that is, regurgitation of blood from left ventricle 28 up into left atrium 24. A lack of sufficient coaptation may be caused by any number of physical anomalies that allow leaflet prolapse (for example, elongated or ruptured chordae 46 and 48, weak papillary muscles 44) or prevent coaptation (for example, short chordae 46 and 48, small leaflets 38 and 40).

Mitral valve insufficiency leads to many complications including arrhythmia, atrial fibrillation, cardiac palpitations, chest pain, congestive heart failure, fainting, fatigue, low cardiac output, orthopnea, paroxysmal nocturnal dyspnea, pulmonary edema, shortness of breath, and sudden death.

There are a number of pathologies that lead to a mitral valve insufficiency including collagen vascular disease, ischemic mitral regurgitation, myxomatous degeneration of leaflets 38 and 40 and rheumatic heart disease.

In ischemic mitral regurgitation (resulting, for example, from myocardial infarction, chronic heart failure), leaflets 38 and 40 and chordae 46 and 48 have normal structure and the mitral valve insufficiency results from altered geometry of left ventricle 28. As a result of ischemia, portions of the heart walls necrose. During healing, the necrotic tissue is replaced with unorganized tissue leading to remodeling of the heart which reduces coaptation through distortion of mitral annulus 34 and sagging of the outer wall of left ventricle 28 which displaces papillary muscles 44.

In FIGS. 3A (top view) and 3B (cross sectional long axis view), The reduction of coaptation resulting from ischemia is depicted for a mitral valve 26 of an ischemic heart 50 that has undergone mild remodeling and suffers from ischemic mitral regurgitation. In FIG. 3B is seen how an outer wall of left ventricle 28 sags outwards, displacing papillary muscles 44 downwards which, through chordae 46 and 48, pulls leaflets 38 and 40 downwards and apart, reducing coaptation. The incomplete closure of mitral valve 26 is seen in FIGS. 3A and 3B.

In some cases, the following progression is observed. Initially, ischemic mitral regurgitation is a minor problem, typically leading only to shortness of breath during physical exercise due to the fact that a small fraction of blood pumped by left ventricle 28 is pumped into left atrium 24 and not through aortic semi-lunar valve 30, reducing heart capacity. To compensate for the reduced capacity, left ventricle 28 beats harder and consequently remodeling continues. Ultimately leaflet coaptation is entirely eliminated as leaflets 38 and 40 are pulled further and further apart, leading to more blood regurgitation, further increasing the load on left ventricle 28, and further remodeling. Ultimately, the left side of the heart fails and the person dies.

Apart from humans, mammals that suffer from mitral valve insufficiency include horses, cats, dogs, cows and pigs.

Currently, it is accepted to use open-heart surgical methods to improve mitral valve functioning by many different methods including: modifying the subvalvular apparatus (for example, lengthening the chordae) to improve coaptation; by implanting an annuloplasty ring, (for example, as described in U.S. Pat. Nos. 3,656,185, 6,183,512 and 6,250,308) to force mitral valve annulus 34 into a normal shape; or by implanting devices in the mitral valve to act as prosthetic leaflets (for example, the United States Patent applications published as US 2002/065554, US 2003/0033009, US 2004/0138745 or US 2005/0038509).

Surgical augmentation of a mitral valve anterior leaflet 38 for improving mitral valve leaflet coaptation for treating ischemic mitral valve regurgitation is taught by Kincaid E H, Riley R D, Hines M H, Hammon J W and Kon N D in Ann. Thorac. Surg. 2004, 78, 564-568. First, an incision is made in the anterior leaflet almost from commissure to commissure. The edges of a roughly elliptical patch of material (for example, bovine pericardium, 1 cm wide by 3 cm long) are sutured to either side of the incision augmenting the anterior leaflet by an amount roughly equal to the surface area of the patch. Additionally, a flexible annuloplasty ring is implanted to reshape the mitral annulus. Although possibly effective, such augmentation is considered a complex surgical procedure performed only by cardiac surgeons having above average skill.

Open heart surgery of any kind is complex, requires long recovery time and is accompanied by a high rate of complications and death. The failure rate of operations for mitral valve function improvement is unacceptably high. Even when successfully performed, persons having undergone such surgeries have an increased chance of infection and stroke, and are often required to use anticoagulant agents for the rest of their lives. Often there is a need to repeat the surgery after a few years.

For these reasons, such procedures are usually tried only when the degree of mitral valve insufficiency is such that death is likely or imminent.

Following a myocardial infarction, the one-year mortality of persons with no ischemic mitral regurgitation is about 6%, with mild ischemic mitral regurgitation about 10%, with moderate ischemic mitral regurgitation about 17% and with severe ischemic mitral regurgitation approximately 40%.

SUMMARY OF THE INVENTION

An aspect of some embodiments of the invention relates to treating ischemic atrioventricular insufficiency by augmenting one or more leaflets of a atrioventicular valve.

In an exemplary embodiment, an atrioventricular valve leaflet is cut, for example punctured, so as that leaflet extends to improve coaptation with the second leaflet.

Optionally, at least one hole is formed in a region referred to as the body of the leaflet, lying at about the center between the valve annulus 34 (FIG. 3a) and the coaptation area 41 (FIG. 3a). A potential advantage of cutting the body of the leaflet is that leaflet flexibility is less affected than if regions at the annulus or at the coaptation area are cut. Optionally, a leaflet portion that is not attached to any of the chordae is selected for cutting, to omit damaging the chordae.

Optionally, the cut is dilated, and tissue from around the cut is pushed by the dilation action further away from the cut, extending the leaflet towards the coaptation area. Optionally, the cut is filled and/or covered to prevent blood from flowing through the cut. Optionally, many small cuts are made. Optionally, the cuts are partial, not going all through the leaflet thickness, thus allowing the leaflet to expand without opening the leaflet to blood flow.

For convenience, the following text refers mainly to the mitral valve, but the aspects, embodiments, and options discussed below are all relevant also to the tricuspid valve, and if modifications are appropriate, they are self-evident to a person skilled in the art of heart surgery.

Thus, in accordance with a first aspect of some embodiments of the invention, there is provided a method of augmenting an atrioventricular valve leaflet, the method comprising:

transcutaneously piercing a leaflet of the valve to at least a portion of the leaflet's thickness to form a pierced section; and extending said leaflet using said pierced section.

Optionally, the antrioventricular valve is a mitral valve.

In an exemplary embodiment the method comprising:

delivering, with a catheter, a piercing element to the vicinity of the valve leaflet; and cutting, with said piercing element, a valve leaflet to at least a portion of the leaflet's thickness so as to allow the leaflet to stretch.

In some embodiments, piercing a leaflet to at least a portion of the leaflet's thickness substantially consists of cutting to a portion of the leaflet's thickness so as to leave one of the leaflet's surfaces intact.

In some embodiments, piercing a leaflet to at least a portion of the leaflet's thickness comprises piercing the leaflet through the entire leaflet's thickness so as to form an opening going through the leaflet from one surface to the other.

Optionally, piercing comprises performing a plurality of discontinuous pierced segments.

Optionally, the method comprises permanently obstructing the opening so as to decrease or prevent blood flow through the opening.

Optionally, the method comprises momentarily obstructing the opening so as to decrease or prevent blood flow through the opening.

Optionally, the method comprises obstructing a plurality of said discontinuous pierced segments with a single obstructor.

In some exemplary embodiments, the method comprises dilating the opening.

Optionally, the method comprises deploying a dilation brace in the dilated opening so as to maintain the dilated opening in a dilated state.

In some exemplary embodiments the method comprises attaching to a surface of an atrioventricular valve leaflet a frame that holds a portion of the leaflet when the heart beats.

Optionally, attaching comprises attaching by suction.

Some embodiments of the invention comprise overlaying a cutting guide on a portion of the leaflet and piercing comprising piercing with the guidance of said cutting guide.

Optionally, the cutting guide comprises a plurality of openings, and piercing comprises piercing through at least one of said openings.

In some exemplary embodiments of the invention piercing comprises:

delivering the piercing device to a first position in the vicinity of the leaflet during a first systole, such that at a first diastole the leaflet hits against the piercing device and is pierced at a first place.

Some embodiments further comprise moving the piercing device to a second position, such that at a second diastole the leaflet hits against the piercing device and cut at a second place.

Another aspect of some exemplary embodiments of the invention concerns a catheter comprising:

a first longitudinal tube having a lumen; and a cutting element extendable from said lumen and adapted for forming a limited cut in a leaflet of an atrioventricular valve.

Optionally, the above catheter comprises a stopper, limiting the depth to which the cutting element can cut.

Optionally, the stopper limits said depth to half the thickness of the leaflet.

Optionally, the catheter comprises a side-movement limiting element, limiting the side movement of the cutting element inside the cut.

In some embodiments, the catheter comprises a second longitudinal tube carrying a frame, configured to attach to said leaflet and stay attached to said leaflet when the heart beats.

An aspect of some embodiments of the invention concerns a catheter comprising:

a first longitudinal tube having a lumen;

a cutting element extendable from said lumen and adapted for forming a cut in leaflet of an atrioventricular valve; and a frame, configured to attach to a leaflet of said atrioventricular valve and stay attached to said leaflet when the heart beats.

Another aspect of some embodiments of the invention concerns a catheter comprising:

a first longitudinal tube having a lumen;

a piercing element extendable from said lumen and adapted for forming a pierced section in a leaflet of an atrioventricular valve; and a cutting guide adapted for deployment on said valve so as to guide the piercing element.

Optionally, the frame attaches to the leaflet by suction.

Optionally, the frame comprises double walls from between which air is sucked, and the frame is reinforced to prevent collapsing of the walls towards each other when said air is sucked.

Optionally, the catheter comprises a cutting guide adopted to overlay on a portion of the leaflet and guiding said piercing element or said cutting element.

Optionally, the cutting guide comprises a plurality of openings, and the piercing element or the cutting element is configured to pierce or cut only through one or more of said openings.

Optionally, the guiding element is integral with the frame.

An aspect of some embodiments of the invention concerns a dilator for dilating a hole in a leaflet of an atrioventricular valve, the dilator comprising:

a body, having:

a closed state, at which the body fits in a catheter and has an upper portion having an upper end, and a lower portion having a lower end, said lower portion connected to the upper portion with at least one joint, and an open state, at which said upper end and lower end are adjacent to each other and said lower portion and upper portion extend perpendicularly to an axis going through said lower and upper ends;

the body being expandable to open against edges of the hole, so as to dilate the hole.

In some embodiments, in the open state, the joints are pressed against edges of the hole.

Optionally, the body comprises a blocking arrangement for blocking blood flow through the dilator in open state.

Optionally, said blocking element is made to block blood pressing against the blocking element at an pressure of 80 mm Hg-120 mm Hg.

In some embodiments, said body comprises hooks that fix the dilator to the tissue around the hole when the dilator is open inside the hole.

An aspect of some embodiments of the invention concerns a kit comprising a catheter according to an embodiment of the invention; and an obstructor for obstructing a cut created by a cutting element of the catheter.

Optionally, the kit comprises an obstructor for obstructing a pierced section created by said cutting element or by said piercing element.

Optionally, the kit comprises a dilator according to an embodiment of the invention.

Optionally, the dilator and the obstructor share one or more components.

Optionally, the dilator and the obstructor are the same.

Optionally, the dilator is carried by a catheter according to an embodiments of the invention.

An aspect of some embodiments of the invention concerns a catheter carrying:

a piercing device; and a dilator according to an embodiment of the invention.

In some embodiments of the invention, the piercing device is configured for forming longitudinal pierced sections having length and width, the length being larger than the width.

In some embodiments, the catheter carries an indication indicating the orientation of said length.

An aspect of some embodiments of the invention concerns a collapsible medical device useful for obstructing holes in tissue such as cardiac valve leaflets, comprising:

a braided tube of metal fabric including a plurality of woven metal strands having a proximal end and a distal end and a longitudinal axis, the braided tube having a substantially tubular collapsed configuration for delivery through a channel and a relaxed configuration having:

a) an axially flattened enlarged diameter distal part having a diameter greater than the diameter of a hole to be blocked;

b) an axially flattened enlarged diameter proximal part having a diameter greater than the diameter of a said hole; and c) a central waist part disposed between and defining a separation distance between said distal part and said proximal part having a length of no greater than about 3 mm wherein the device is configured for deployment in a hole in a cardiac valve leaflet.

Optionally, the device further comprises a deployment adaptor associated with said distal end, configured to engage an elongated deployment component passing coaxially through said braided tube.

An aspect of some embodiments of the invention concerns a catheter useful for augmenting a cardiac valve leaflet comprising:
- a) an elongated shaft having a longitudinal axis extending between a proximal end and a distal end thereof;
- b) near a distal tip of said elongated shaft, a dilation component configured to dilate a hole in tissue configured to deploy a dilation brace and an obstruction component in a said hole.

In some embodiments, the catheter further comprises a piercing component at a distal tip of said elongated shaft configured to pierce tissue located.

Optionally, said piercing component is configured to pierce cardiac leaflet tissue.

An aspect of some embodiments of the invention concerns a method of augmenting a cardiac valve leaflet comprising:
- a) piercing a cardiac leaflet of a heart to produce a hole;
- b) placing a dilation component in said hole;
- c) dilating said hole by activating said dilation component; and
- d) deploying a dilation brace in said hole so as to maintain said hole in a dilated state.

Optionally, the method further comprises
- e) obstructing said hole.

Optionally, the method further comprises
- f) deploying a mitral valve annulus supporting device.

In some embodiments, the piercing of said cardiac leaflet is performed with the help of a catheter-borne piercing element.

Optionally, prior to said piercing, said catheter-borne piercing element is brought into proximity with said cardiac leaflet through a trans-septal puncture.

Optionally, said hole is dilated to a diameter of at least about 3 mm.

Optionally, said hole is dilated to a diameter of at least about 4 mm.

Optionally, said hole is dilated to a diameter of at least about 5 mm.

Optionally, said dilation is performed over a period of no more than about 5 minutes.

Optionally, said dilation is performed over a period of no more than about 2 minutes.

Optionally, said dilation is performed over a period of no more than about 1 minute.

In some embodiments, the dilation component is an inflatable balloon.

In some embodiments, the dilation component is a catheter-mounted inflatable balloon.

In some embodiments, the dilation brace is an expandable ring.

Optionally, deploying of said dilation brace is performed with the help of a catheter.

In some embodiments, said dilation of said hole and said deploying of said dilation brace is substantially simultaneous.

Optionally, said dilation brace comprises an expandable ring mounted on said dilation component during said dilating.

In some embodiments, obstructing said hole is substantially simultaneous with said deploying of said dilation brace.

In some exemplary embodiments, said hole is substantially round subsequent to said dilating.

In some embodiments of the invention, the heart is beating when the hole is dilated.

In exemplary embodiments the cardiac leaflet or the atrio-ventricular leaflet is a miteral valve leaflet, optionally a posterior leaflet of the mitral valve.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 4A-4K depict steps of an embodiment of the method of the present invention for augmenting a posterior mitral valve leaflet;

FIGS. 5A-5B are schematic illustrations of an obstructor useful as dilation braces according to an exemplary embodiment of the invention;

FIG. 6A depicts the distal end of a catheter of the present invention useful for implementing the teachings of the present invention.

FIG. 8 is a schematic illustration of a mitral valve having a plurality of non-obstructed holes according to an exemplary embodiment of the invention;

FIG. 9A is a schematic illustration of a mitral valve during puncturing with the aid of a valve holder according to an embodiment of the invention;

FIGS. 9B and 9C are schematic illustrations of frames according to exemplary embodiments of the invention.

DESCRIPTION OF EXEMPLARY EMBODIMENTS

Overview

The present invention, in some embodiments thereof, relates to the field of cardiac medicine and more particularly but not exclusively to mitral valve leaflet augmentation.

An aspect of some embodiments of the invention relates to treating ischemic mitral insufficiency (also known as ischemic mitral regurgitation) by augmenting one or both of the mitral valve leaflets.

In an exemplary embodiment, a mitral valve leaflet is cut, optionally with a cut of non-zero size, so as to allow the leaflet to extend and/or stretch and occupy a larger surface, wherein at least some of the larger surface is at the coaptation area. Optionally, the cut is filled and/or covered to prevent blood from flowing through the cut. Optionally, many small cuts are made. Optionally, the cuts are partial, not going all through the leaflet thickness, thus allowing the leaflet to stretch without opening the leaflet to blood flow.

Figures 3A, 3B:
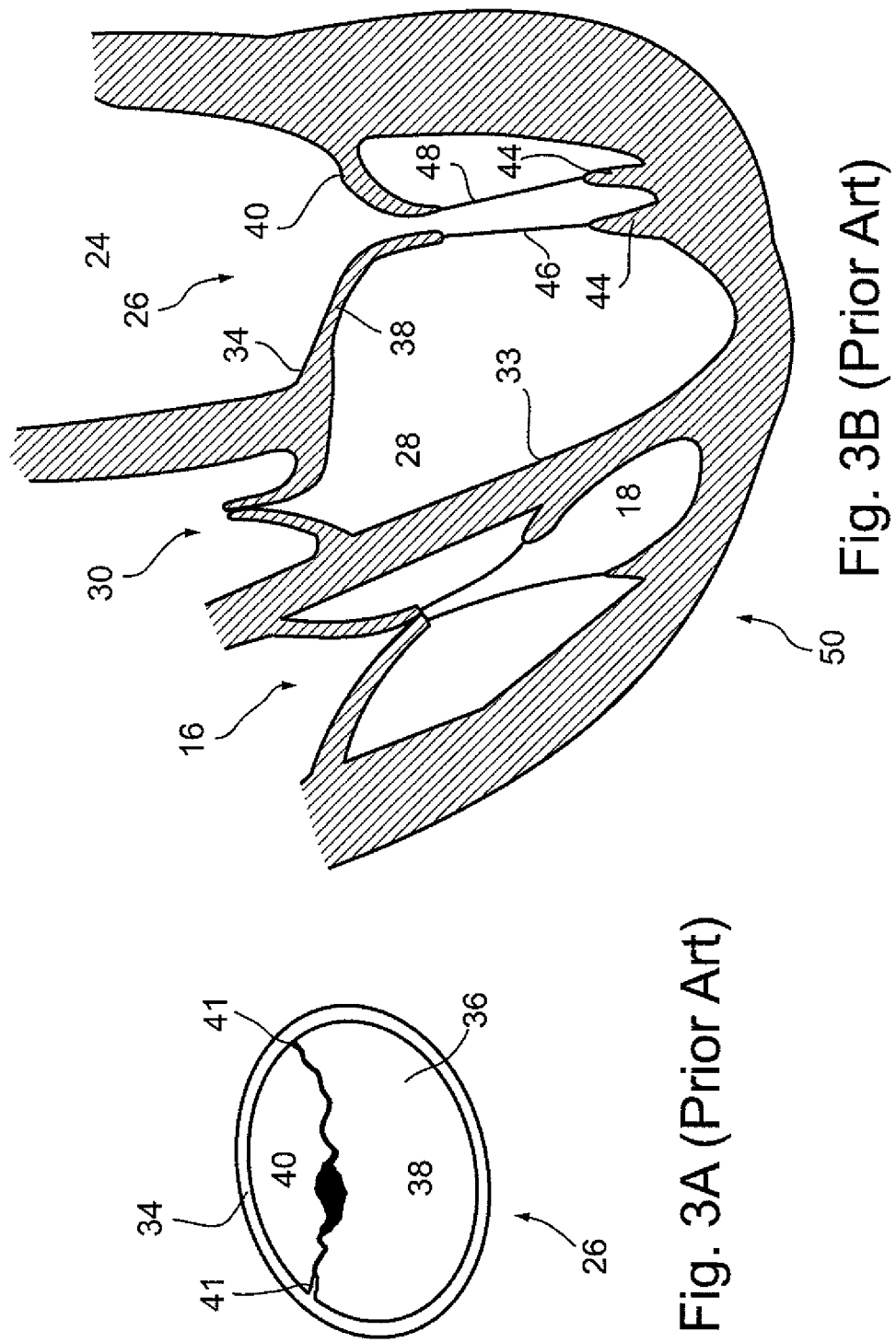
FIGS. 3A and 3B (prior art) are schematic depictions of parts of a heart with mild ischemic mitral regurgitation related to incomplete coaptation of the leaflets of the mitral valve.
Figure 3C:
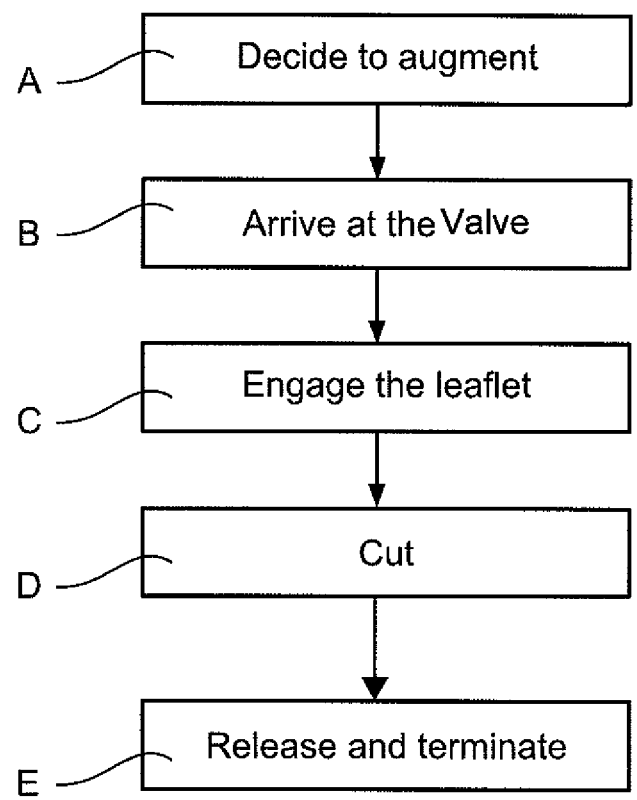
FIG. 3C is a flowchart showing actions taken in a mitral valve augmentation method according to an exemplary embodiment of the invention.

FIG. 3C is a flowchart showing actions taken in a mitral valve augmentation method according to an exemplary embodiment of the invention.

At A, the patient is diagnosed, and a decision is made to proceed with mitral valve augmentation. Optionally, the decision includes a decision to carry out the leaflet augmentation transcutaneously. The transcutaneous route may be preferred in case of patients with harder conditions, that have a high risk not to tolerate an open heart surgery.

At B, a catheter is brought the vicinity of the mitral valve, optionally, as described below under the heading "Exemplary minimally invasive routes to the mitral valve".

At C, a mitral valve leaflet is engaged, so as to facilitate cutting or piercing the leaflet while the heart is beating.

At D, a mitral valve is cut at one or more places. Optionally, both leaflets are cut.

At E, the leaflet is released, and the operation terminated.

Some embodiments of the invention relates to catheters and hole obstructors useful in implementing methods according to embodiments of the present invention.

The present invention, in some embodiments thereof, is based on the realization that when a hole is created in a mitral valve leaflet, the leaflet material around the hole does not bunch up or tear. Rather, the leaflet stretches outwards, substantially remaining constant in surface area, but larger in perimeter. As a result, the area covered by the leaflet increases, in embodiments up to about the sum of the area of the hole and the original area of the leaflet. As a result, the leaflet is augmented. In embodiments the augmentation of the leaflet increases coaptation of the leaflets of the valve.

Thus, some embodiments of the present invention allow a mitral leaflet to be augmented and are useful for treating a condition where cardiac valve leaflet augmentation is useful, such as mitral valve insufficiency, for example, ischemic mitral regurgitation.

The term treating a condition is used to denote any of: curing the condition, treating the condition, preventing the condition, treating symptoms of the condition, curing symptoms of the condition, ameliorating symptoms of the condition, treating effects of the condition, ameliorating effects of the condition, and preventing results of the condition.

Optionally, cardiac valve leaflet augmentation is performed invasively. Alternatively, augmentation is performed minimally-invasively using one or more catheters.

Minimally-invasive methods are known to be cheaper, safer, quicker and require less post-procedure care than open heart procedures.

Some embodiments of the present invention are safer and quicker than known valve augmentation methods; therefore, the present invention may be applied to subjects who are suffering from only mild ischemic mitral regurgitation or even with only reduced leaflet coaptation accompanied by no clinically insignificant mitral regurgitation. In such instances, leaflet augmentation in accordance with some embodiments may stop (and in embodiments even reverse) cardiac remodeling and deterioration of the condition of the subject from that of mild ischemic mitral regurgitation to moderate and severe ischemic mitral regurgitation.

An aspect of some embodiments of the present invention concerns a method of augmenting a cardiac valve leaflet, which optionally increases the degree of coaptation of the leaflet with another leaflet. In an exemplary embodiment the method comprises: a) piercing the cardiac leaflet to produce a hole; b) placing a dilation component in the hole; c) dilating the hole by activating the dilation component so as to increase the surface of the cardiac leaflet as discussed above; d) deploying a dilation brace in the dilated hole so as to maintain the dilated hole in a dilated state. Optionally, the dilation brace is implanted in the hole to stay in the hole permanently. In embodiments, also e) obstructing the dilated hole, for example to prevent subsequent substantial passage of liquid such as blood through the hole.

Optionally, the piercing of the cardiac leaflet is performed with the help of a catheter-borne piercing element such is known in the art of cardiac surgery, for example, a trocar.

Exemplary Minimally Invasive Routs to the Mitral Valve

When arriving at the mitral valve transcutaneously, several routes are possible. The different routes differ in the way traveled in the body to the valve, and in the side of the valve that is approached.

Optionally, prior to piercing the leaflet the catheter-borne piercing element is brought into proximity with the atrial side of the leaflet and the piercing is from the atrial side out through the ventricular side of the leaflet. Alternatively, the catheter-borne piercing element is brought to proximity with the ventricle side of the leaflet, and the piercing is from the ventricle side up into the atria.

Routes to the Atrial Side of the Valve

Optionally, the catheter is guided through the venous system (for example, from the jugular vein or femoral vein) into the right atrium. A transspetal puncture is made between the right and left atrium, and the catheter goes through the puncture to the left atrium.

Optionally, the catheter is guided through the arterial system (for example, entry from the femoral artery) into the aorta, and from the aorta to the left ventricle in accordance with standard procedures.

Routes to the Venticular Side of the Valve

In some embodiments, the catheter is guided through the venous into the right atrium, through a transseptal puncture, through the mitral valve orifice and turned around in a "J" shape in accordance with standard procedures.

In some embodiments, the catheter is guided through the arterial system (for example, from the femoral artery) into the aorta and left ventricle, through the mitral valve orifice and turned around in a "J" shape in accordance with standard procedures. In embodiments, the ventricular side of the mitral valve is accessed using a catheter penetrating the apex of the heart into the left ventricle.

In some embodiments, some other approaches, which are also less invasive than open surgery are used, for example, keyhole approach.

Exemplary Obstructions of the Hole(s)

In some embodiments, a device known in the art is used as an obstructor for obstructing one or more holes produced in the mitral valve leaflet in accordance with some embodiments of the present invention.

Some suitable obstructors include Amplatzer® Septal Occluder (AGA Medical Corporation, Plymouth, Minn., USA); Amplatzer® Membranous VSD Occluder; and devices fashioned in accordance with the teachings of U.S. Pat. Nos. 5,725,552; 5,944,738 and 5,846,261.

In an exemplary embodiment, the obstructor includes two components: an outer resilient shape-memory fabric (for example, of titanium-nickel alloy wires, Nitinol) as a skeleton; and at least one sealing layer (for example, of polyester fabric). Optionally, the sealing layer is inner to the skeleton. The skeleton is configured to have a collapses state and a relaxed state. In the collapsed state the obstructor fits into a flexible tube shape to allow delivery with the help of a guide wire or catheter; and in the relaxed state, the obstructor has dumbbell shape having two axially flattened parts associated through a waist.

Subsequent to deployment, both the skeleton and the sealing layer reduce blood flow therethrough. In some embodiments, the sealing layer acts as a cell growth matrix allowing new leaflet tissue to grow through the layer to seal the obstructor entirely. In some embodiments, the sealing layer is designed such that any flow of blood through the obstructed hole is ultimately prevented.

In some embodiments, a hole is obstructed with a fabric overlaying the hole on the ventricular side of the leaflet, and kept in place by the blood pressure. Optionally, the fabric has small hooks that help fixing the fabric to the leaflet.

In some embodiments, the holes made in the leaflet are small enough not to allow significant blood flow therethrough, and obstructing the small holes may be omitted. For instance, in some cases, holes of about 2 mm to 4 mm in size may be left not obstructed without causing significant mitral insufficiency. In some cases, some insufficiency is initially caused, and then cured by blood coagulation and/or tissue growth at the holes.

In some embodiments, larger holes are formed in the leaflet, and they are obstructed to limit or eliminate any blood flow through the holes, as described above.

Optional Hole Dilatation

Optionally, the holes are large enough not to close back, but small enough not to allow significant blood flow therethrough. Optionally, some the holes are formed and/or shaped such that significant blood flow occurs through the holes immediately after the holes are formed, and stops after a while, when the holes are clogged by blood coagulation. Holes that may be formed with a piercing element and do not require dilatation include longitudinal holes of 2-4 mm in length, optionally parallel to the coaptation area between the two leaflets may have suitable shape and size.

In some embodiments, the pierce or cut is perpendicular to the leaflet. In some embodiments, the pierce or cut is not perpendicular to the leaflet. Optionally, a non-perpendicular cut allows more stretching of the leaflet than a perpendicular one of the same size. Optionally, blood flow through a non-perpendicular cut is less severe than through a perpendicular one.

In some exemplary embodiments a hole in the valve leaflet is dilated. Dilatation of the hole may be advantageous in pushing more tissue towards the coaptation area, thus improving coaptation.

Optionally, one hole is formed in the leaflet, and is dilated to a diameter of about 10-15 mm. Optionally, a plurality of holes, for instance, 2, 3, or 4 holes are formed in a leaflet, and one or more of them is dilated to a diameter of about 3 mm-7 mm.

Figure 5D:
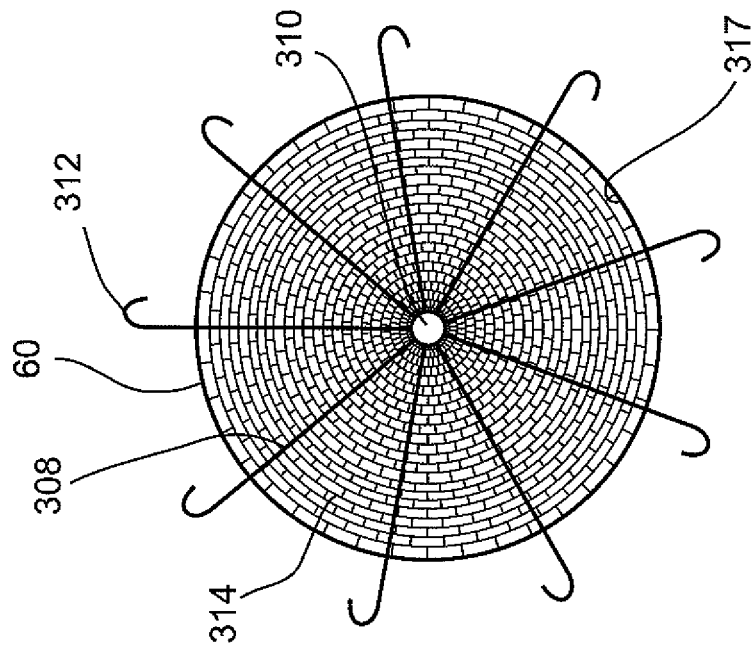
FIG. 5D is a schematic illustration of a top view of a hole 60 dilated and obstructed with a dilator according to an embodiment of the invention.
Figure 5C:
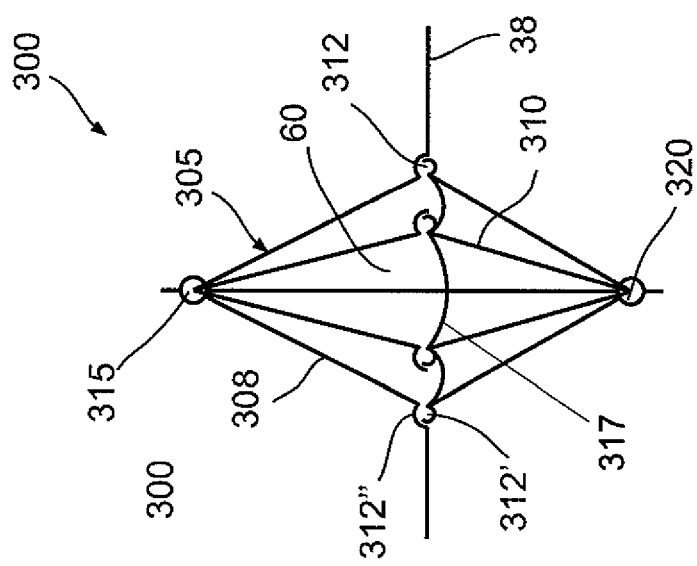
FIG. 5C is a schematic illustration of a dilator for dilating a hole in a mitral valve leaflet according to an embodiment of the invention.

Dilation of a hole in the cardiac leaflet is optionally performed with the help of catheter-borne dilation components such as known in the art of minimally-invasive cardiologic intervention, and or dilators according to embodiments of the present invention, for instance, as depicted in FIG. 5C. Suitable dilation components include but are not limited to prior art catheter-borne balloons, such as angioplasty balloons (especially non-compliant balloons such as the Ultra-thin™ SDS Balloon Dilatation Catheter from Boston Scientific Company, Natick, Mass., USA.

Optionally, prior to piercing the leaflet the catheter-borne dilation component is brought into proximity with the leaflet through a trans-septal puncture in accordance with standard procedures. (See action B at FIG. 3C and the section headed "Exemplary minimally invasive routs to the mitral valve")

Optionally, the transseptal puncture is through the intraatrial septum and the dilation component placed in the hole from the atrial (top) face of the mitral valve. In some embodiments, the transseptal puncture is through the intraventricular septum and the dilation component is placed in the hole from the ventricular (bottom) face of the mitral valve.

In an exemplary embodiment the dilation component is configured to dilate the hole so that the dilated hole is substantially round, for example as with an angioplasty balloon. That said, in some embodiments, the dilation component used may be configured to dilate the hole so that the dilated hole has another shape, for example, elliptical, oval or ovoid. The shape of the dilated hole is optionally selected to fit the desired change in the leaflet shape, such that the leaflet will improve its coaptation with the second leaflet. Optionally or additionally, the shape is selected as to stay away from leaflet portions that are preferably left untouched, for example, the chordae. In some embodiments, dilation of the hole is performed over a period of no more than about 5 minutes, no more than about 2 minutes or no more than about 1 minute.

In some embodiments, activation of the dilation component to dilate the hole is performed when the beating of the heart is arrested. In some embodiments, activation of the dilation component to dilate the hole is performed when the heart is beating.

In some embodiments, the hole is dilated to a diameter of at least about 3 mm (9 French) augmenting the area of the leaflet by up to about 7 $mm^2$. It is noted that not all the area of the hole(s) is necessarily helpful in improving coaptation between the leaflets. For example, in some embodiments tissue stretches in directions other than required for improving the coaptation. In some embodiments, about 30%-50% of the area of the hole(s) is effective in improving the coaptation. Other exemplary dilations of the hole are to a diameter of at least about 4 mm, 5 mm, 10 mm, or 14 mm augmenting the area of the leaflet by up to about 12 $mm^2$, 19 $mm^2$, 78 $mm^2$, and 154 $mm^2$, respectively.

In some embodiments, a dilation brace is deployed after or substantially simultaneously with dilation of the hole, to maintain the hole in a dilated state and to prevent the dilated hole from substantially closing. Although any suitable dilation brace may be deployed in the dilated hole, in some embodiments the dilation brace is an expandable ring, for example, expandable ring analogous to a short stent of between 1 mm and 2 mm length. Optionally, the dilatation ring is capable of applying pressure of from about 10 atmospheres to about 30 atmospheres, for instance, about 20 atmospheres.

In some exemplary embodiments, a dilation brace is deployed with the help of a catheter such is known in the art of cardiac surgery. Prior art catheters suitable for deploying a dilation brace in accordance with some embodiments include but are not limited to prior art catheter-borne balloons, for example angioplasty balloons. In embodiments utilizing such prior art dilatation brace, the dilation brace is optionally mounted on the dilation component, the dilatation component with mounted dilation brace is placed in the hole, and then the dilation component is activated to dilate the hole as described above and to substantially simultaneously deploy the dilation brace inside the hole.

Optionally, such dilatation may be considered similar to the deployment of a stent during an angioplasty procedure, however, the present dilatation process is different from stent deployment in many aspects. For example, a stent is usually deployed in a cylindrical blood vessel, and not in a hole in flat tissue. As another example, the blood vessel is usually muscular and smooth, while a mitral valve leaflet is more cartilage-like. As another example, in blood vessels there may be issues of plaque fracturing, which are irrelevant to most embodiments of the present invention. Another example, stents are not deployed with their ends curling over, as is the case in some embodiments of the invention.

In some embodiments, prior to deployment of the dilation brace the catheter-borne dilation brace is brought in proximity with the leaflet from the ventricular side of the leaflet (for example, through a transseptal puncture), as discussed above.

In some embodiments, prior to deployment of the dilation brace the catheter-borne dilation brace is brought in proximity with the leaflet from the atrial side of the leaflet (for example, through a transseptal puncture), as discussed above, and the dilation brace is placed in the hole from the atrial (top) face of the mitral valve. Arterial routes may have several advantages over ventricular routes. For instance, an arterial route, especially if going from the jugular vein, is shorter than getting to the valve from the ventricular side. In some cases, it is easier to follow the procedure with Doppler ultrasound imaging from the arterial side, and there is less chance that the catheter will interfere with the chordae.

Optionally, one or more of the devices used in an augmentation procedure according to some embodiments of the invention are brought to the valve from the ventricular side, and one or more—from the atrialarterial side.

In some exemplary embodiments of the invention a plurality of small holes are formed in the leaflet, and they are not dilated. Some such embodiments are discussed in relation to FIG. 8 below.

An Exemplary Augmentation Process

FIGS. 4A-4K schematically illustrate a mitral valve in various stages of an augmentation process according to an exemplary embodiment of the invention. The embodiment depicted in FIGS. 4A-4K is optionally performed using only prior art devices.

In FIG. 4A, heart 50 suffers from minor ischemic mitral regurgitation resulting from incomplete coaptation of anterior leaflet 38 and posterior leaflet 40 of mitral valve 26. The gap between the two leaflets is illustrated as a dark area 41.

In FIG. 4B, with the beating of heart 50 arrested, a guide wire 52 is introduced through a femoral vein through the superior or inferior vena cava into heart 50 to right atrium 12. Using, optionally, standard procedures, the septum between left atrium 24 and right atrium 12 is punctured and a cannula 54 placed in the puncture to serve as a conduit allowing access to left atrium 24. Guide wire 52 is passed through cannula 54 to proximity with the upper surface of anterior leaflet 38 of mitral valve 26.

Figure 4C:
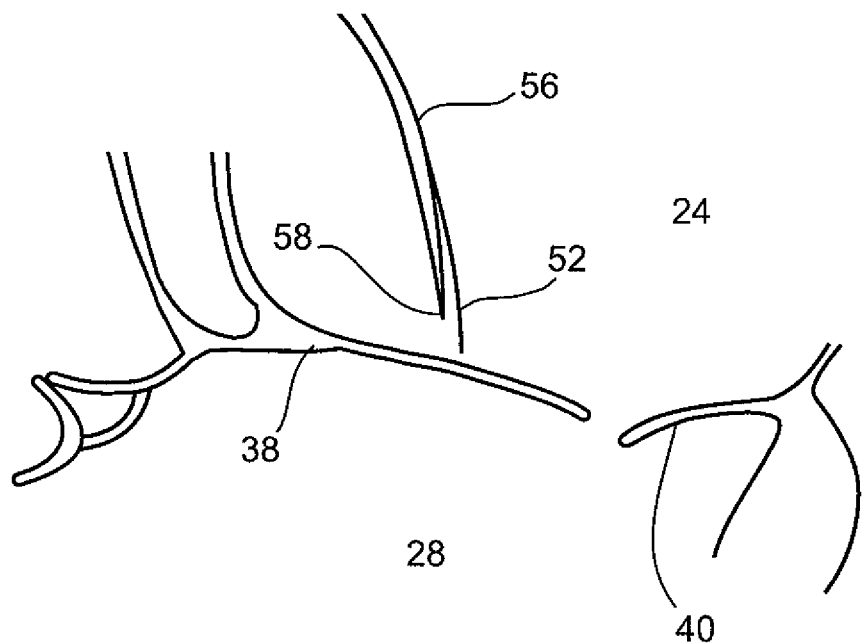

In FIG. 4C, a catheter 56 with a hollow trocar as a piercing element 58 is advanced along guide wire 52.

Figure 4D:
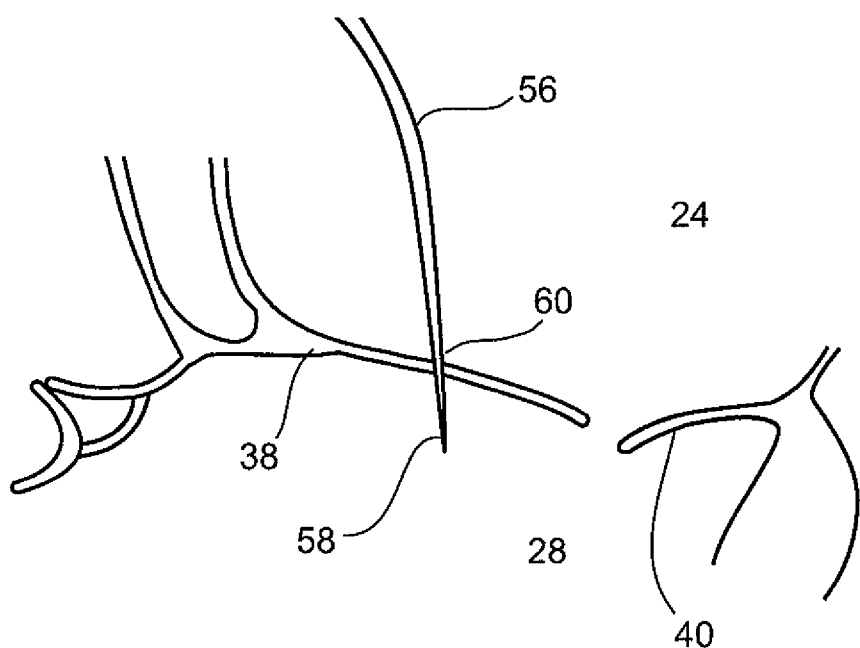

In FIG. 4D, piercing element 58 of catheter 56 is used to pierce anterior mitral leaflet 38, making a hole 60. Guide wire 52 (See FIG. 4C) is passed through the lumen made by piercing element 58 to emerge on the ventricular side of anterior leaflet 38. After cutting, piercing element 58 is withdrawn.

Figure 4E:
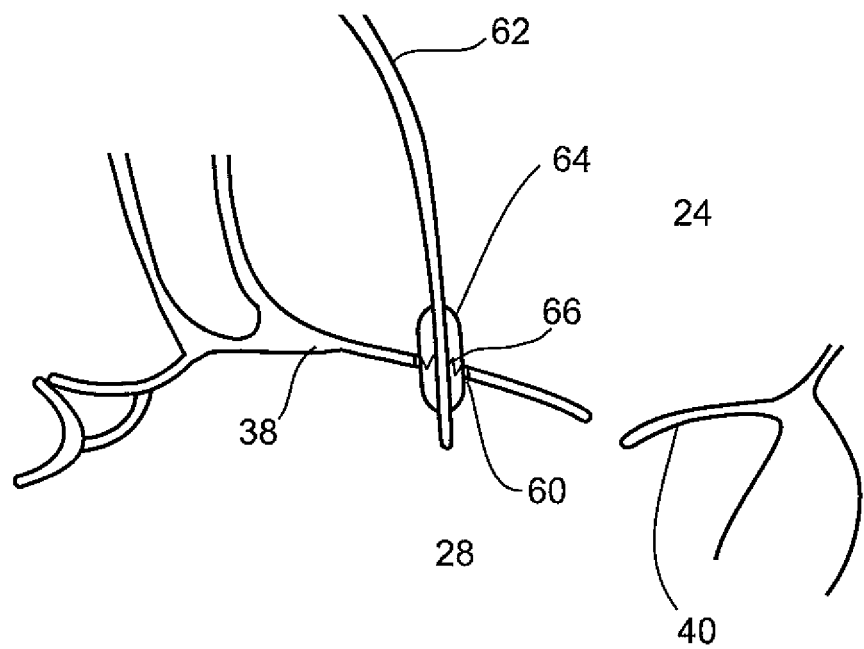

In FIG. 4E, an angioplasty catheter 62 (for example Ultrathin™ SDS Balloon Dilatation Catheter from Boston Scientific Company, Natick, Mass., USA) bearing an inflatable angioplasty balloon 64 as a dilation component onto which a dilation brace 66 (a 2 mm long expandable ring analogous to a short stent) is crimped is advanced along guide wire 52 and pushed through hole 60.

Figure 4F:
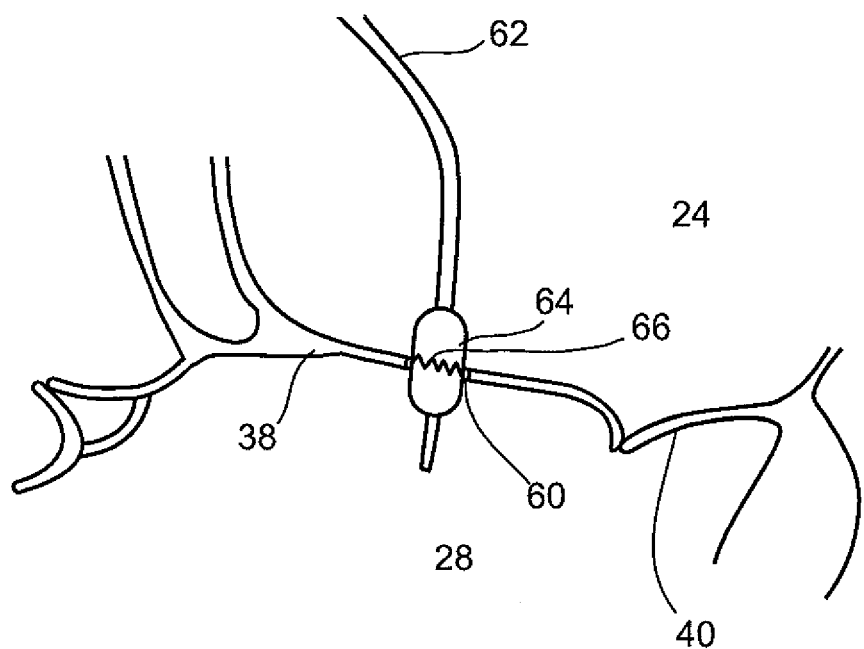

In FIG. 4F, balloon 64 of angioplasty catheter 62 is expanded, for example with inflation medium. Balloon 64 and dilation brace 66 are expanded, optionally for a period of about 45 seconds, and consequently hole 60 dilated to a circular diameter of about 5 mm (15 French) and an area of about 19 mm². During the expansion, the area of posterior leaflet 38 also increases by approximately 19 mm², increasing coaptation of posterior leaflet 38 with anterior leaflet 40, closing gap 41 (FIG. 4A) between leaflets 38 and 40, preventing further reflux of blood from left ventricle 28 into left atrium 24. Balloon 64 is deflated and angioplasty catheter 62 withdrawn.

Figure 4G:
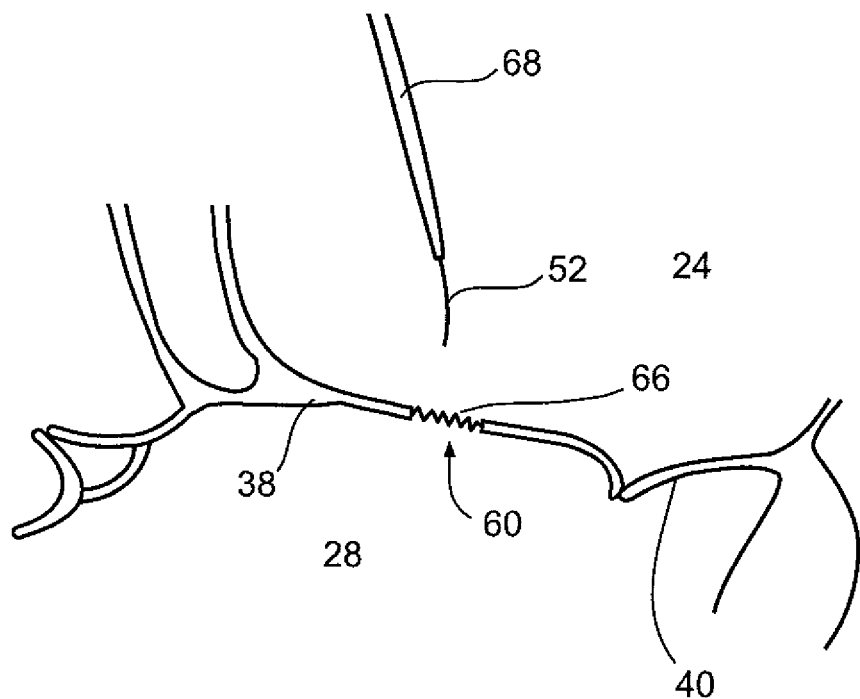

In FIG. 4G, hole 60 remains dilated due to the presence of dilation brace 66. An obstructor deployment catheter 68 (for example, a hollow tube, optionally a delivery catheter of 7 French outer diameter and 6 French inner lumen diameter) is advanced along guide wire 52.

Figure 4H:
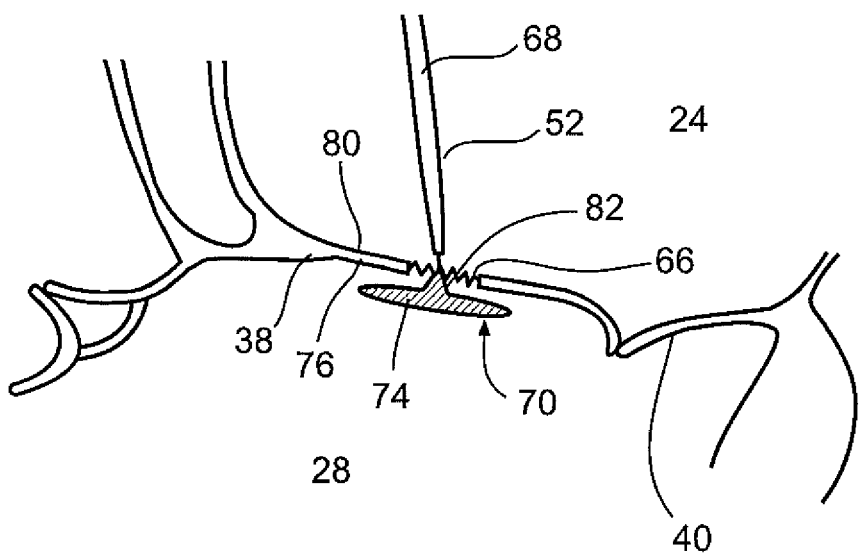

In FIG. 4H, guide wire 52 is withdrawn and an expandable obstructor 70 (for example, an Amplatzer® Septal Occluder from AGA Medical Corporation, Plymouth, Minn., USA, see below) is pushed through the lumen of obstructor deployment catheter 68 into dilated hole 60 with an obstructor delivery wire 72 (See FIG. 4I), optionally, in a manner similar to that described in U.S. Pat. No. 5,725,552. Obstructor deployment catheter 68 is pulled back, allowing a distal part 74 of expandable obstructor 70 to expand out into an 8 mm diameter disk shape on a ventricular side 76 of leaflet 38.

Figure 4I:
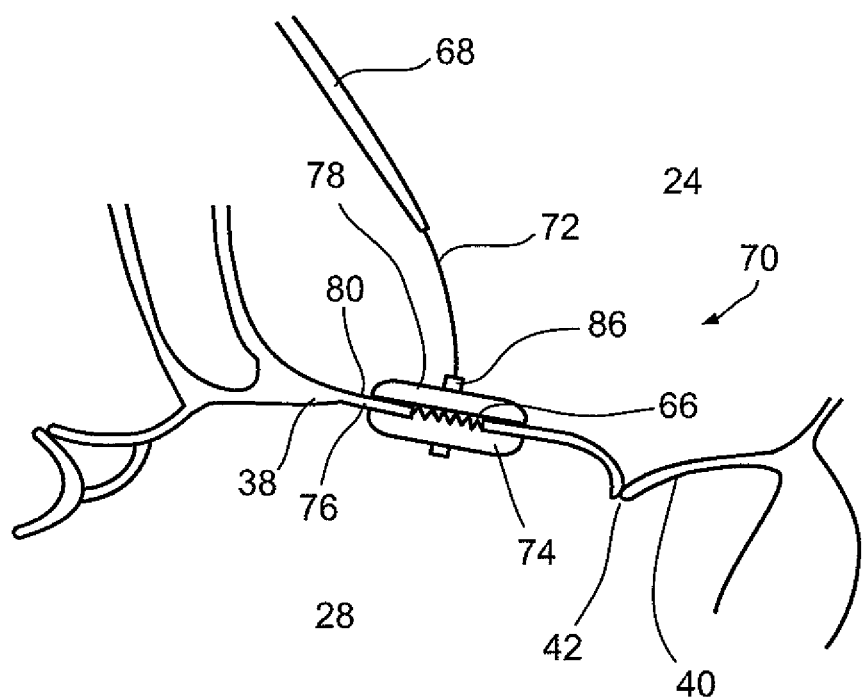

In FIG. 4I, obstructor deployment catheter 68 is pulled further back, allowing a proximal part 78 of expandable obstructor 70 to expand out into an 8 mm diameter disk shape on an atrial side 80 of leaflet 38 so as to clamp both sides of dilation brace 66 while a waist 82 (FIG. 4H) of expandable obstructor 70 is located in the bore of dilation brace 66, thus substantially sealing dilated hole 60. Obstructor delivery wire 72 is detached (for example, unscrewed) from deployment adaptor 86 of expandable obstructor 70 and withdrawn. Cannula 54 is removed, and the procedure completed appropriately as understood by one skilled in the art.

Optionally, the size and/or shape of the flattened portions is selected so as not to interfere with adjacent chordae, and/or to match the shape of the leaflet. In some embodiments, the flattened parts are not circular. For example, in some embodiments they are shaped to parallel the borders of the leaflet.

Optionally, before choosing an obstructor of a specific size and/or shape, the valve is imaged, and the obstructor is chosen responsive to leaflet shape and/or chordae location.

FIGS. 4J and 4K schematically illustrate mitral valve 26, after anterior leaflet 38 is augmented to coapt exterior leaflet 40, in the process described in FIGS. 4A to 4I. FIG. 4J illustrates a top view of the mitral valve, and FIG. 4K illustrates a front view of the mitral valve inside the heart.

The figures schematically show how expandable obstructor 70 and dilation brace 66 are deployed in leaflet 38 to maintain dilation of hole 60 and prevent leakage of blood therethrough, and how augmentation leads to an improved area of coaptation 42 of leaflets 38 and 40.

In the above-described method, hole 60 is obstructed substantially simultaneously with the deployment of dilatation brace 66.

In some embodiments, the dilation brace is distinct from the obstructor, such that the dilatation brace and the obstructor used to obstruct a hole produced according to embodiments of the present invention comprise at least two distinct components. For example, a stent portion with an Amplatz™ device.

In some embodiments, the dilation brace and the obstructor comprise at least one shared component. In some embodiments, the dilation brace and the obstructor are substantially the same.

In the embodiment described above with reference to FIGS. 4A-4I, dilation brace 62 and obstructor 66 are distinct components and are deployed separately. In some embodiments, a dilation brace and an obstructor are deployed substantially simultaneously. In some embodiments, a dilation brace and an obstructor share at least one component. In some embodiments, a dilation brace and an obstructor are a single component.

Exemplary Obstructors

An aspect of some embodiments of the invention relates to a collapsible medical device, useful for obstructing a hole in tissue such as cardiac valve leaflets. In the following such a device will be referred to as an obstructor.

In one exemplary embodiment the obstructor comprises a tubular section having a collapsed state, configured for delivery through a channel (such as of a catheter) and a relaxed state, configured for obstructing a hole in a cardiac valve leaflet by deployment therein.

In the relaxed state, the device has: a) an axially flattened distal part having a diameter greater than the diameter of the hole; b) an axially flattened proximal part having a diameter greater than the diameter of the hole; and c) a central waist part disposed between and defining a separation distance between the distal part and the proximal part. The central waist part optionally has a length of about 3 mm or less. Optionally, the diameter of one or both of the flattened parts is between about 5 mm and about 18 mm.

Optionally, the tube section is formed as a braided tube including a plurality of woven strands each having a proximal end and a distal end. Optionally, the braided tube is made of metal fabric. Optionally, the ends are fashioned so as to inhibit unraveling of the braid.

For ease of use and deployment, it is preferred that the flattened distal and proximal parts have an inherent tendency to adopt the relaxed configuration. In some embodiments this tendency is temperature dependent, and in some embodiments this tendency is temperature independent.

Optionally, the flattened end portions have shape memory properties. Optionally, the waist part does not have shape memory properties. Alternatively, the waist part has shape memory properties.

Obstructing

Optionally, the tube section is braided with wires that are dense enough to function as a skeleton, giving the obstructor the desired shape. In some embodiments, the wires making up the skeleton are not dense enough to sufficiently prevent the flow of blood therethrough. Optionally, such embodiments comprise obstructing components, configured to obstruct the axial flow of a liquid such as blood through the obstructor. In some embodiments, the additional obstructing component is contained within the obstructor's skeleton.

Optionally, the obstructing component comprises fibers. Optionally, the fibers are woven. Optionally, the fibers are woven into a sheet and/or a tube. Optionally, the fibers are randomly arrayed. Optionally, the obstructing component is non-woven. Some examples of materials suitable for making obstructing components include polyesters, polyamides, Nylon, and Dacron, or other materials used to hinder or prevent blood flow.

Thickness of Flattened Parts

Preferably, the flattened distal and proximal parts are as thin as possible so as to interfere as little as possible with leaflet movement and flexing and with blood flow through the cardiac valve orifice. Thus, in some embodiments the thickness (axial dimension) of each of the distal and proximal parts is no greater than about 1 mm, optionally no greater than about 0.5 mm.

Diameter of Flattened Parts

The diameter (radial dimension) of both the flattened distal and proximal parts is preferably sufficient to completely obstruct a hole in a cardiac leaflet dilated in accordance with some embodiments of the present invention. In some exemplary embodiments, the diameter is from about 5 mm up to about 18 mm. Optionally, the diameter of both flattened parts is greater than the diameter of the hole to be obstructed. In some exemplary embodiments, the diameter of the flattened part is larger than the hole by at least about 1 mm, at least about 2 mm or at least about 3 mm. Optionally, the diameter of the flattened parts at the two sides of the leaflet is the same.

Generally, the surgical approach by which the obstructor is deployed determines which of the two flattened parts of an obstructor is deployed atrially and which ventricularly. In the embodiment depicted in FIG. 4, where obstructor 70 is deployed with the help of delivery wire 72 approaching cardiac leaflet 38 from the atrial side 80, distal part 74 of obstructor 70 is deployed ventrically and proximal part 78 is deployed atrially. In some embodiments, configured for deployment from the ventricular side, the obstructor is delivered with its larger flattened part proximally to the smaller flattened part.

Deployment Adaptor

Optionally, for ease of manipulation and deployment, an obstructor is provided with a deployment adaptor (see, for instance, part 68 in FIG. 5A), a component configured to engage a delivery device (for example, delivery wire 72). In some embodiments, a deployment adaptor is secured to or near the proximal part of the obstructor, such as known in the art and described for obstructor 70 in FIG. 4. In some embodiments, (discussed below), a deployment adaptor is located at the distal end of an obstructor and is configured to engage a delivery device, such as delivery wire or catheter shaft, that passes coaxially through the obstructor.

Length of Waist Part

In the relaxed configuration, the waist part of an obstructor optionally defines a parallel walled tube coaxial with the axis of the obstructor. The separation distance between the flattened distal and proximal parts is at least partially determined by the length (axial dimension) of the waist part. The length is preferably such that the waist part is entirely contained within the dilated hole and the distal and proximal parts substantially clamp the cardiac leaflet close to the edge of the dilated hole. Such clamping maintains the obstructor in place and assists in maintaining a leak-proof seal around the dilated hole. As the central portion of a mitral valve leaflet is typically approximately between 0.3 and 1.0 mm thick the length of a central waist part of an obstructor configured for use in augmenting a mitral valve leaflet is optionally no more than about 1 mm, no more than about 0.8 mm, no more than about 0.6 mm, no more than about 0.4 mm or less than about 0.3 mm. The efficacy of such clamping is increased by providing the flattened distal and proximal parts with a substantially concave surface facing the waist part side of the respective part.

Diameter of Waist Part

In some exemplary embodiments, the obstructor is configured to function as a dilation brace. Optionally, the obstructor comprises a waist part configured to function as a dilation brace. For example, in some embodiments the obstructor is sufficiently wide so as to contact and support the edge of a dilated hole.

Optionally or additionally, the obstructor is firm enough not to collapse as a result of an inwards force applied by the edges of a dilated hole. Optionally, the obstructor central part is expandable, optionally self expandable. Optionally, an obstructor with an expandable central part is useful for dilating a hole: the obstructor is positioned with the central part at the hole, and expanded to dilate the hole. In some such embodiments, outer and inner parts that cover the hole from outside may be omitted.

In some embodiments, the obstructor includes a waist part reinforced against inwards collapse, for example where the wires making up the waist are thicker than the wires making up the distal and proximal parts of the obstructor. In some embodiments, the waist part diameter is large enough to facilitate centering of the obstructor. For instance, in some embodiments, the waist part diameter is larger than 90% of the hole diameter.

In some embodiments, the waist part is build to stand pressure of about 10, 20, or 30 atmospheres, so it can dilate the holes mainly by its own, without an additional dilation brace.

In some exemplary embodiments, a waist part of an obstructor expands up to some maximal diameter. Optionally, the waist part self-expands. Optionally, a waist part functions similarly to a self-expanding stent, made of a shape-memory alloy. In such embodiments, the waist part of the obstructor expands to the diameter of the dilated hole and maintains that diameter. In some embodiments, to expand the waist part, an outwards radial force is applied to the inside surface of the waist part, for example by a catheter-mounted balloon or another deployment member. Optionally, the diameter of the waist part increases to the extent determined by the balloon.

In some exemplary embodiments, the waist part has an outer diameter that is smaller than the outer diameter of both the flatted distal part and proximal part. Optionally, the waist part is smaller than the smallest of the distal and proximal flattened parts in about 1 mm to about 4 mm.

The length (axial dimension) of the waist is optionally between about 0.5 and 2 mm, for instance, between about 0.8 mm and 1.5 mm. For comparison, in some embodiments the thickness (axial dimension) of the flattened proximal part and distal part is about 1 mm or less, for instance, less than about 0.6 mm.

An obstructor 84 according to an exemplary embodiment of the invention is depicted in a relaxed configuration in FIG. 5A, in cross-section. Obstructor 84 is made of braided 0.127 mm thick Nitinol wires. Obstructor 84 is optionally collapsible to form a along tube of braded Nitinol. Optionally, the dimensions of the collapse obstructor are suitable for delivering the obstructor with a deployment catheter such as catheter 68, described above. Optionally, the deployment catheter has internal diameter of 6 French (2 mm), and the collapsed obstructor has an outer diameter of 5 French. Optionally, in the collapsed state, obstructor 84 is about 12.5 mm long.

As depicted in FIG. 5A, in a relaxed configuration the obstructor 84 has a proximal part 78, with optionally convex proximal face. Optionally, proximal part 78 has a diameter D78 (radial dimension) of 8 mm, and thickness T78 (axial dimension) of 0.5 mm.

Distally from proximal part 78 obstructor 84 adopts the shape of a waist part 82. Optionally, waist part 82 has a diameter D82 of 6 mm (radial dimension) and thickness T82 of 1 mm (axial dimension).

Distally from waist part 82, obstructor 84 has a distal part 74, with optionally convex distal face. Optionally, distal part 74 has a diameter D74 (radial dimension) of 8 mm, and thickness T74 (axial dimension) of 0.5 mm.

At the proximal end of proximal part 78 shown is a deployment adaptor 86 secured to proximal part 78. Optionally, deployment adaptor 86 functions to hold together the proximal ends of the strands making up the braided tube so as to prevent unraveling.

Optionally, at the distal end of distal part 74 is a button 88 which functions to hold together the distal ends of the strands making up the braided tube so as to prevent unraveling. Optionally, strands of polyester fibers 90 are contained within the inner volume of the braided tube to improve the obstruction provided by obstructor 84.

FIG. 5B is a schematic illustration of a cross-section in an obstructor 92 according to an exemplary embodiment of the invention. Obstructor 92 is similar to obstructor 84 but further comprises a deployment adaptor 86 located at the distal end of obstructor 92 and configured to allow a delivery device, such as catheter shaft 94 to pass coaxially through obstructor 92 to engage deployment adaptor 86 as depicted in FIG. 5B and as is discussed below.

In obstructor 92, proximal end 78 is shown provided with a ring 96 to define a passage for a delivery device such as catheter shaft 94 and to hold together the proximal ends of the strands making up the braided tube so as to prevent unraveling. Other components related to catheter shaft 94 and depicted in FIG. 5B are discussed below.

As mentioned above, in some embodiments the obstructor and the dilator share one or more elements. In some embodiments a single element functions both as dilator and as an obstructor.

An exemplary element that may be used as a dilator, as an obstructor, or as both a dilator and an obstructor is schematically illustrates in FIG. 5C.

FIG. 5C is a schematic illustration of a dilation component 300 according to an exemplary embodiment of the present invention. Dilator 300 is shown in a hole 60 in a mitral valve leaflet 38.

Dilator 300 has a closed state, at which it fits into a catheter lumen, and an open state, at which it has an umbrella-like shape, with the outer diameter of the umbrella dilating hole 60. In operation, the obstructor is put in the hole when the obstructor is in the closed state, and positioned in the hole such that when the device is opened, the umbrella will open to dilate the hole without sliding to the atrial or ventricular side of the leaflet.

Dilator 300 comprises a body 305 and an opening mechanism 310.

In the embodiment shown, body 305 comprises a plurality of rods or wires 308, all of which are tied at poles 315 and 320, and connected at their center with a wire 317. Each rod is made of two portions, tied together at the middle with a joint, such that when the poles come together, the joints move apart from each other to obtain an umbrella-like shape, and dilate hole 60. When the device is extended, wire 317 interfaces with hole 60. Near each joint there are shown two hooks 312, made to stick into leaflet 38, one from below (for instance, 312') and one from above (for instance 312").

Body 305 is optionally self-expanding. Alternatively or additionally, body 305 is expandable when force is applied thereto. Optionally, this force is applied by a balloon expanded inside device 300 to expand body 305. Optionally, an opening mechanism 310 is used.

Opening mechanism 310 is optionally operable to shorten so as to bring poles 315 and 320 together so as to dilate hole 60. Optionally, after device 300 is fully deployed, opening mechanism 310 is locked, optionally, using locking methods known in the art, as, for examples, those used for locking Amplatzer™ devices.

In an exemplary embodiment, dilator 300 is made to apply on the edges of hole 60 pressure of between about 10 and 30 atmospheres, for example, about 15-20 atmospheres.

FIG. 5D is a schematic illustration of a top view of a hole 60 dilated and obstructed with a dilator similar to dilator 300 of FIG. 5C. The figure shows wires 308 dilating hole 60 and hooks 312 fixing dilator 300 to the upper surface of leaflet 38. The Figure also shows opening mechanism 310 at its locked state.

In an exemplary embodiment of the invention, the rods forming the umbrella are elastically connected at one point, and when released, self-expand to dilate the hole. In such an embodiment, a distinct opening mechanism may be omitted.

In the embodiment shown in FIG. 5D a fine mesh 314 is stretched between rods 312 to obstruct blood flow through the device. Optionally, mesh 314 blocks or reduces blood flow pressing against it at pressures of about 100 mm-120 mm Hg above atmospheric pressure.

Embodiments of a Delivery Catheter

The augmentation procedure depicted in FIGS. 4A-4I can be preformed in open surgery or transcutaneously. Both ways may benefit from carrying the procedure as fast as possible, to allow quick termination of the invasion into the heart and its surrounding.

In some cases, the use of prior art devices only, necessitates that steps of the method be done serially. To facilitate mitral valve augmentation according to some embodiments of the invention, some novel devices are described herein.

An aspect of some embodiments of the present invention relates to a delivery device configured to allow substantially simultaneous performance of some of the actions taken in the process depicted in FIGS. 4A-4I. Such simultaneous performance optionally allows augmenting a mitral valve leaflet faster than when the actions are performed serially. Optionally, the simultaneous performance of actions facilitates augmenting a mitral valve leaflet according to some embodiments of the invention, when the heart is beating.

Specifically, in some embodiments, dilation of a produced hole and obstruction of the dilated hole are performed substantially simultaneously, optionally on a beating heart. Such a delivery device is optionally used for deployment of obstructors according to some embodiments of the invention, for example, obstructor 92 depicted in FIG. 5B.

In some embodiments, a delivery device according to an embodiment of the invention comprises a dilation component (such as an inflatable balloon) configured to deploy a dilation brace and to deploy an obstruction component.

Optionally, a distinct dilatation brace is omitted. Omitting a distinct dilatation brace can be achieved, for instance, when the obstruction component also functions as a dilation brace. An example of such an obstruction component is depicted in FIG. 5B as obstructor 92.

Optionally, a delivery device further comprises a piercing element to produce a hole in a cardiac leaflet.

Thus, in some exemplary embodiments, the present invention provides a catheter useful for minimally-invasively augmenting a cardiac valve leaflet. Such catheter optionally comprises: a) an elongated shaft having a longitudinal axis extending between a proximal end and a distal end; and b) near the distal end of said elongated shaft, a dilation component (for example, an inflatable balloon) configured to dilate a hole in tissue. Optionally, the catheter is configured to deploy a dilation brace and an obstruction component in such a hole.

In some embodiments, the dilation brace and the obstruction component share one or more components. In some embodiments, the dilation brace and the obstruction component are parts of substantially the same component.

In some embodiments, the catheter further comprises a piercing component, configured to produce a hole in tissue (for example, cardiac leaflet tissue).

Exemplary Dilating and Obstructing Processes

In FIGS. 6A-6G is depicted a distal end of a delivery device according to an exemplary embodiment of the present invention.

FIG. 6A is a schematic illustration of a distal end of a catheter 98. Catheter 98 is configured to pierce a cardiac leaflet to produce a hole in the cardiac leaflet, dilate the hole and deploy an obstructor such as obstructor 92 to act as a dilation brace and obstruct the hole. Using catheter 98 in accordance with some exemplary embodiments of the invention, a cardiac leaflet may be augmented quickly, optionally, while the heart is beating.

Catheter 98 comprises an outer slidable sheath 100, optionally having a 9 French (3 mm) internal bore. Parallel to slidable sheath 100 is a guide wire tube 102 defining a guide wire channel for use with a standard cardiac guide wire such as guide wire 52 (see FIG. 4C).

Coaxial with slidable sheath 100 is a balloon catheter shaft 94 through which passes a fluid transport channel 104 in fluid communication with a balloon 64. Balloon 64 is a 3 mm long non-compliant balloon allowing accurate inflation up to at least 5 mm in diameter with no substantial "dog boning". The distal end of balloon catheter shaft 94 is tipped with piercing element 58 of stainless steel. Just distal to balloon 64 is a tubular obstructor enclosure 108 coaxial with catheter shaft 94, opening out in a distal direction to surround a portion of catheter shaft 94 and connected to catheter shaft 94 through enclosure base 110.

In the substantially tubular volume delimited by catheter shaft 94, enclosure base 110, obstructor enclosure 108 and slidable sheath 100 is held obstructor 92 described in FIG. 5B constrained to a collapsed, tubular conformation. Obstructor 92 includes a proximal ring 96, a deployment adaptor 86 and fibers constituting additional obstructing components 90.

Engaging deployment adaptor 86 are two pawls 112 which are components of an obstructor locking mechanism. The obstructor locking mechanism also a notched piston 114 and a fluid channel 116.

A guide wire 52 is brought into proximity of an anterior leaflet 38 of a mitral valve substantially as described in FIG. 4B.

In FIG. 6A, catheter 98 is guided along guide wire 52 to proximity with atrial side 80 of anterior mitral valve leaflet 38.

Figure 6B:
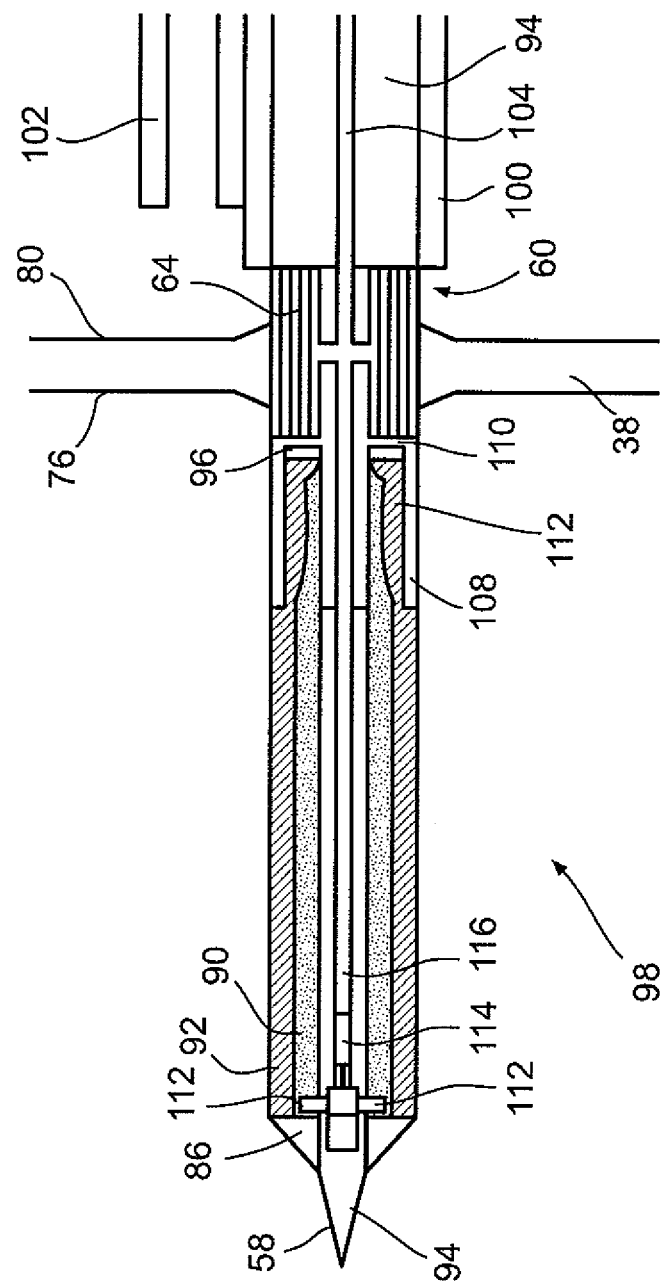
FIGS. 6B-6G depict a method according to an exemplary embodiment implemented by deploying the obstructor of FIG. 5B in an anterior leaflet with the help of the catheter depicted in FIG. 6A.

In FIG. 6B, catheter shaft 94 is pushed forward relative to slidable sheath 100 against atrial side 80 of leaflet 38, piercing leaflet 38 and producing a hole 60. Catheter shaft 94 is pushed through hole 60 until balloon 64 is located in hole 60 (optionally about 17 mm). Released from the constraint imposed by sliding sheath 100, obstructor 92 tends to the relaxed configuration depicted in FIG. 5B, pulling deployment adaptor 86 tightly against pawls 112. The bases of pawls 112 contact notched piston 114 fixing the notched piston so as to prevent obstructor 92 from adopting the relaxed configuration.

Figure 6C:
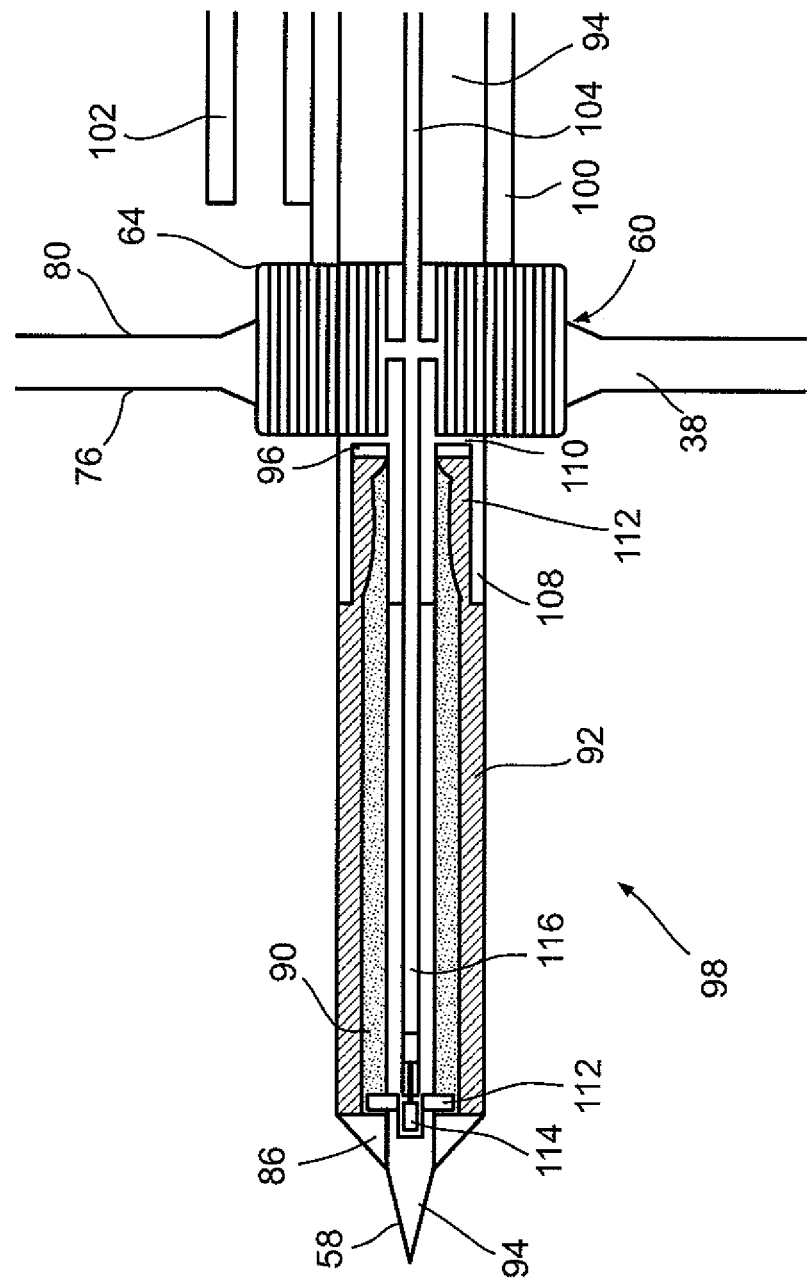

In FIG. 6C, balloon 64 is inflated by introduction of fluid such as saline through fluid transport channel 104 dilating hole 60. In such a way, leaflet 38 is augmented in accordance with an exemplary embodiment of the present invention. The fluid also passes through fluid channel 116, pushing notched piston 114 distally so that the notches in notched piston 114 are across pawls 112. The pressure applied by deployment adaptor 86 forces pawls 112 into the notches, releasing obstructor 92 from constraints on configuration.

Figure 6D:
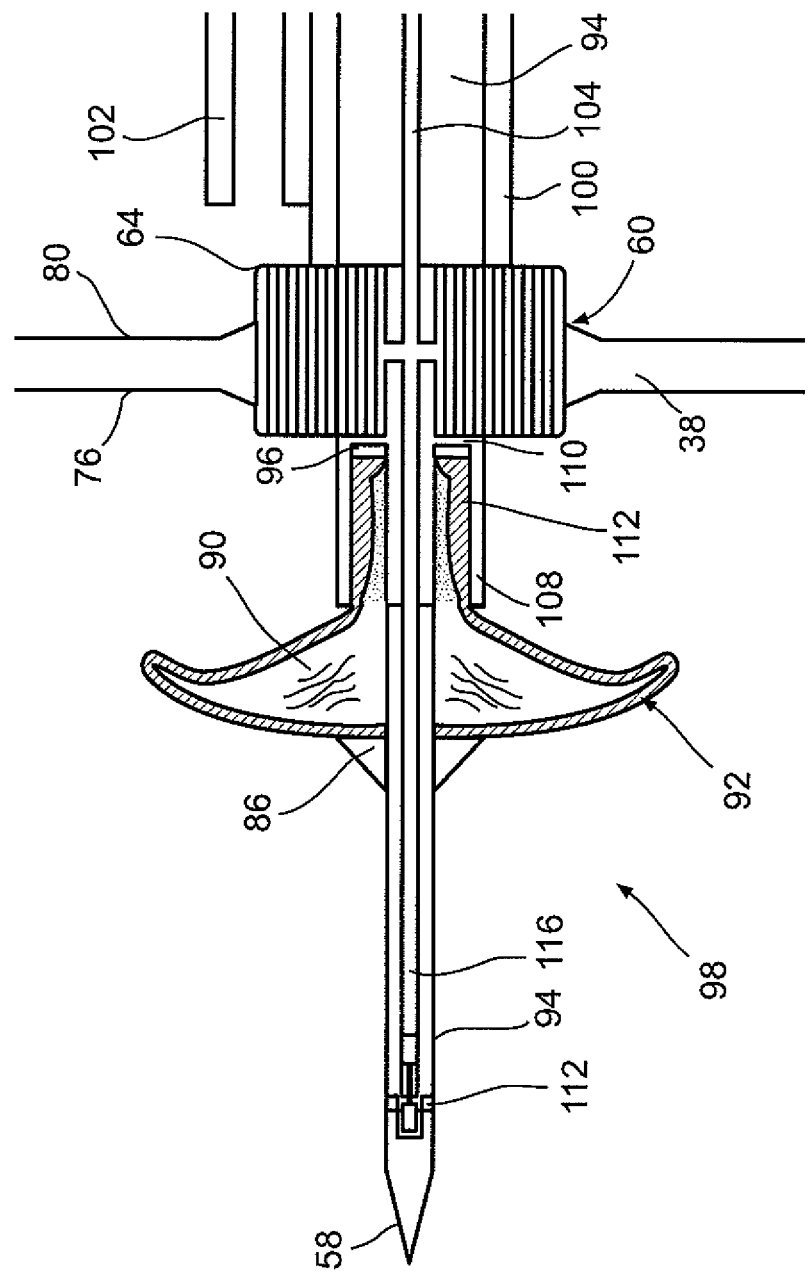

In FIG. 6D is seen how the release of the constraints by pawls 112 allows obstructor 92 to relax towards a relaxed configuration as deployment adaptor 86 slides proximally along catheter shaft 94. Obstructor 92 does not relax fully as the proximal end of obstructor 92 is contained within enclosure 108.

Figure 6E:
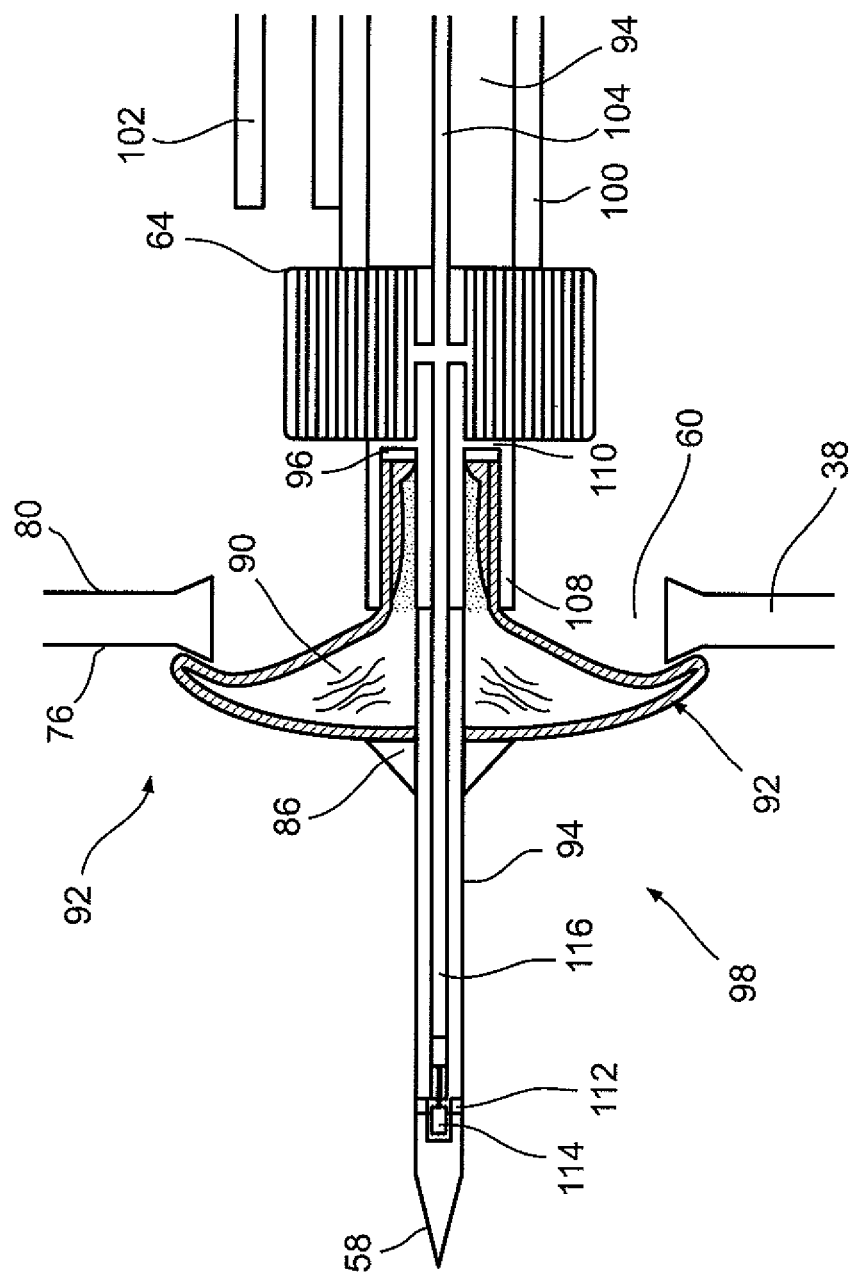

In FIG. 6E, catheter 98 is pulled proximally so that balloon 64 exits and obstructor 92 enters hole 60.

Obstructor 92 contacts ventricular side 76 of leaflet 38. Further pulling of catheter 98 pulls the proximal end of obstructor 92 from enclosure 108, allowing obstructor 92 to adopt a completely relaxed configuration, where distal part 74 and proximal part 78 have a flattened shape (FIG. 6F).

Figure 6F:
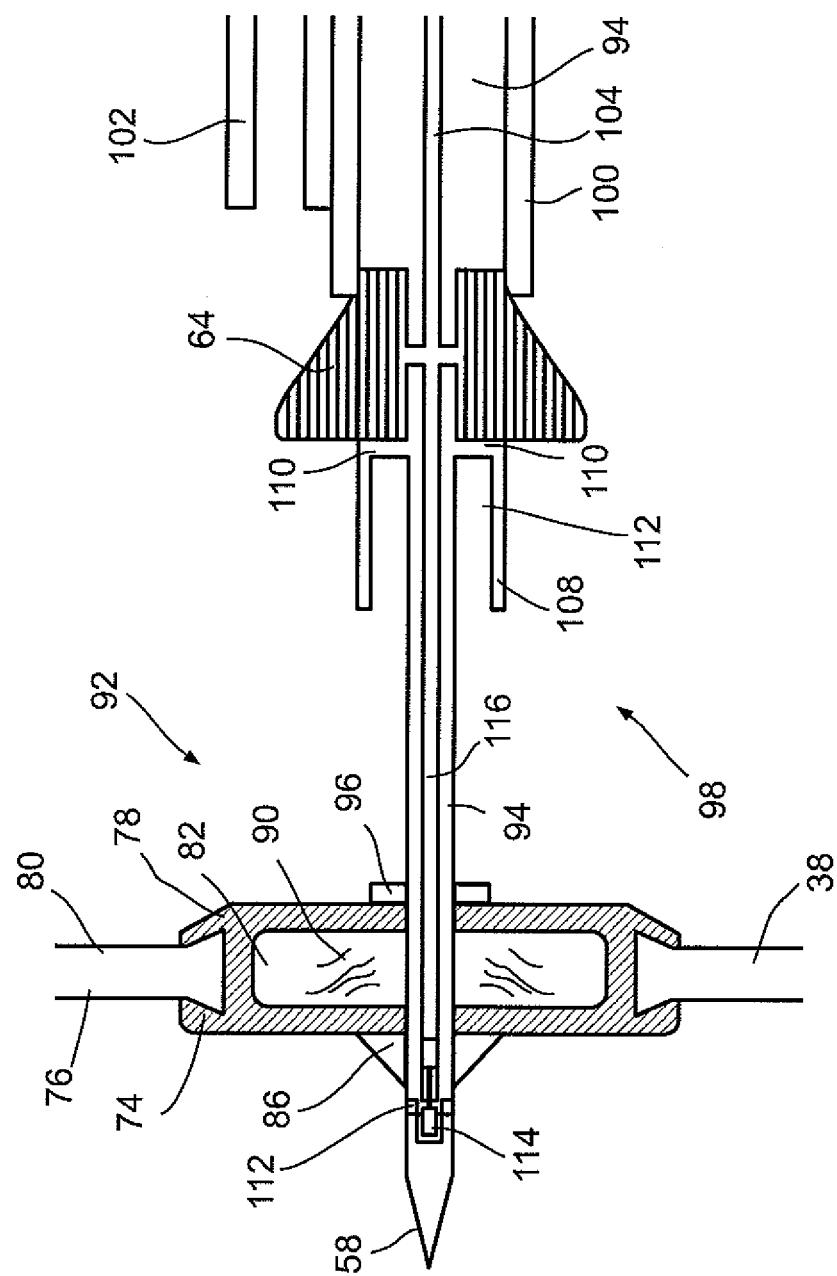
Figure 6G:
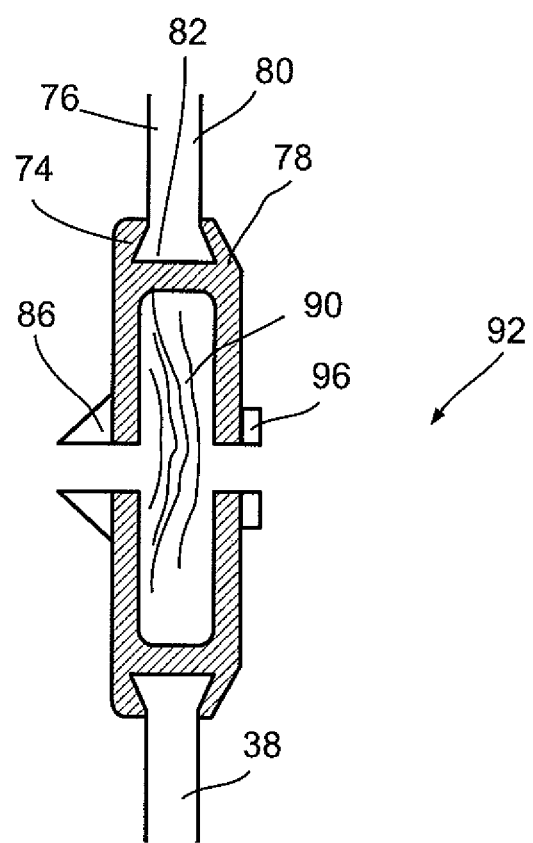

In FIG. 6F, obstructor 92 is in a fully relaxed configuration where leaflet 38 is clamped between distal part 74 on ventricular side 76 and proximal part 78 on atrial side 80. Waist part 82 of obstructor 92 presses against the edges of hole 60, acting as a dilation brace to prevent closure of hole 60. The distal (concave) face of proximal part 78 of obstructor 92 presses against atrial side 80 while the proximal (concave) face of distal part 74 of obstructor 92 presses against ventricular side 76 making a leak proof seal.

Catheter 94 is withdrawn from the subject and the procedure completed in the usual way. Strands of additional obstructing component 90 float into the axial passage of obstructor 92 through which catheter 94 passed, obstructing the passage. The wires making up obstructor 92 together with the strands of the additional obstructing component 90 substantially reduce the passage of blood through obstructor 92. In some embodiments, the passage of blood through obstructor 92 is reduced even further by the injection of a substance, such as biological glue, into obstructor 92 through a tube, which is optionally guided along guide wire 52.

In some embodiments, an additional obstructing component comprises strands of fabric that are mutually associated and/or associated with the braided tube, for example, with one or more of the distal part, proximal part, and waist part so that relaxation to the relaxed configuration stretches the strands across the axial passage.

The above-described method includes accessing the mitral valve from above with a catheter passing through the atrial septum. In some embodiments of the invention, the mitral valve is accessed from above using a retrograde (transaortic) approach for any one or more of the steps of the method.

In some embodiments, the mitral valve is accessed from below with a catheter passing through the ventricular septum for any one or more of the steps of the method.

In some embodiments, a mitral valve annulus supporting device such as an annuloplasty ring is deployed in addition to augmentation of the valve leaflet, whether prior or subsequent to deploying of the dilation brace.

In some exemplary embodiments, the mitral valve annulus supporting device is deployed minimally-invasively. Suitable minimally-invasively deployed mitral valve annulus supporting devices are described, for example, in PCT Patent Applications published as WO 02/30295, WO 02/30298 and WO 05/112827 and in US patent applications published as US 2003/0074012, US 2006/129188, US 2006/229717 and US 2006/0184242.

The present invention has been described herein primarily implemented as a minimally-invasive, catheter-based procedure. It is understood, however, that some embodiments of the present invention may be carried out in an invasive surgical procedures. For example, in some embodiments, the method is implemented as described in Kincaid E H, Riley R D, Hines M H, Hammon J W and Kon N D in Ann. Thorac. Surg. 2004, 78, 564-568, with or without the deployment of an annuloplasty ring as described therein, where augmentation is not performed by slitting a leaflet and attaching a patch thereto, but rather with the use of a dilation component substantially as described hereinabove.

The present invention has been described herein primarily with reference to augmentation of the anterior mitral leaflet as embodiments of the present invention are useful in treating ischemic mitral regurgitation, a common pathological condition. It is understood that the teachings of the present invention are useful in treating other pathological conditions where augmentation of a mitral valve leaflet is useful. A typical example is augmentation of an anterior mitral valve leaflet to treat systolic anterior motion of the anterior mitral valve leaflet that occurs, for example, with hypertrophic obstructive cardiomyopathy.

Figure 1:
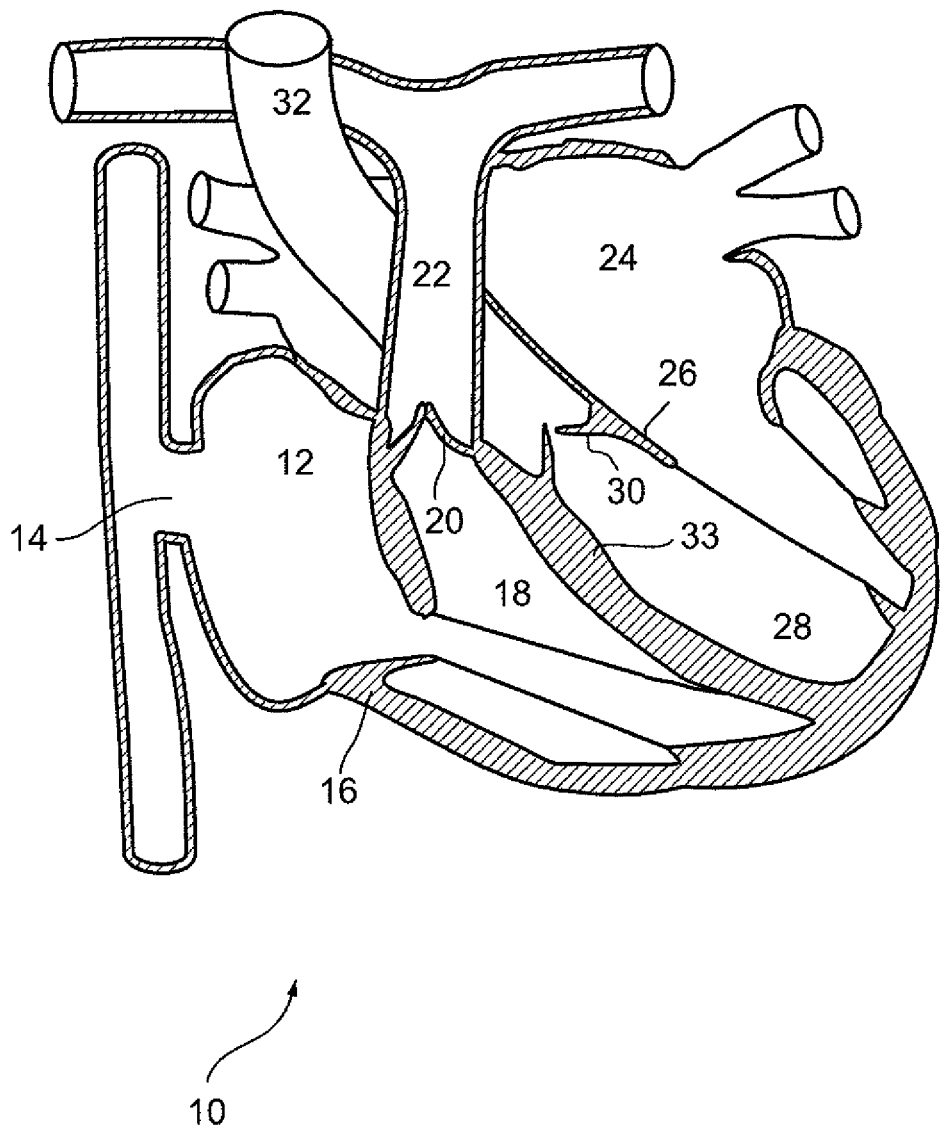
FIG. 1 (prior art) is a schematic depiction of a healthy heart in cross section.

In hypertrophic obstructive cardiomyopathy, septum 33 (FIG. 1) undergoes unusual growth and thickening into left ventricle 28. In up to about 50% of cases there is dynamic left ventricular obstruction produced by narrowing of the left ventricular outflow tract and by systolic anterior motion of mitral valve leaflets 38 and 40 against septum 33. A number of mechanisms are implicated in causing the systolic anterior motion of the leaflets. In one mechanism, the narrowing of the outflow tract leads to a higher blood flow velocity (Venturi effect) between the septum and leaflets, causing the leaflets to move anteriorly. In another mechanism, the bulge of septum 33 caused by the hypertrophy changes the flow of blood out of the ventricle so that the edges of leaflets 38 and 40 in coaptation region 42 are found in the systolic out flow at an angle that pulls the leaflets apart leading to mitral regurgitation and into the left ventricular outflow tract. In another mechanism, papillary muscles 44 are displaced, allowing leaflets 38 and 40 to enter the systolic out flow. Thus, despite the fact that annulus 34, leaflets 38 and 40 and chordae 46 and 48 are all patent, the force applied by the outflow on the coaptation edge of anterior leaflet 38 is such that the leaflets are pulled apart and anterior leaflet 38 is moved towards septum 33, leading to left ventricular outflow tract obstruction.

Typical treatments of hypertrophic obstructive cardiomyopathy include: septal myectomy (to remove the bulge of septum 33 into left ventricle 28); anterior leaflet 38 plication (to stiffen anterior leaflet 38); anterior leaflet 38 augmentation (to stiffen anterior leaflet 38 and shift coaptation depth 42 out of the systolic outflow), replacement of mitral valve 26 with a low-profile valve, the Alfieri procedure, mobilization and partial excision of papillary muscles 44 and/or alcohol septal ablation.

Figure 2B:
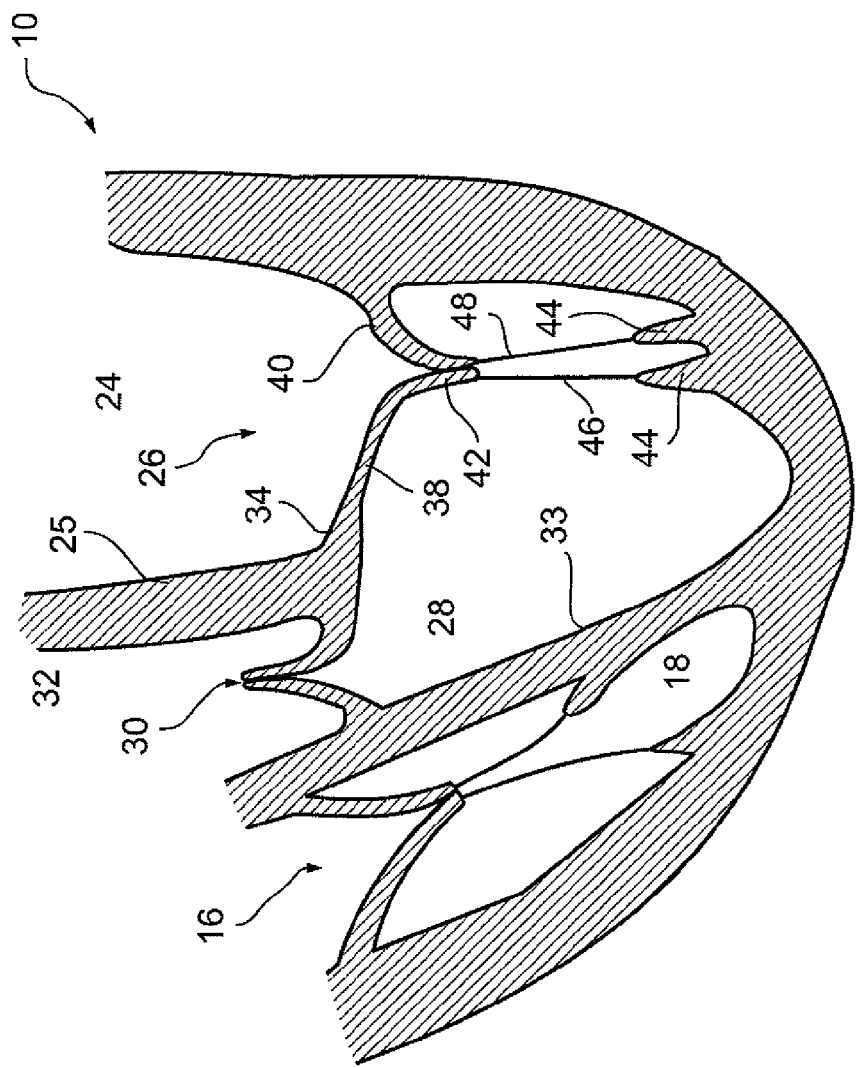
FIGS. 2A and 2B (prior art) are schematic depictions of parts of a healthy heart.
Figure 2A:
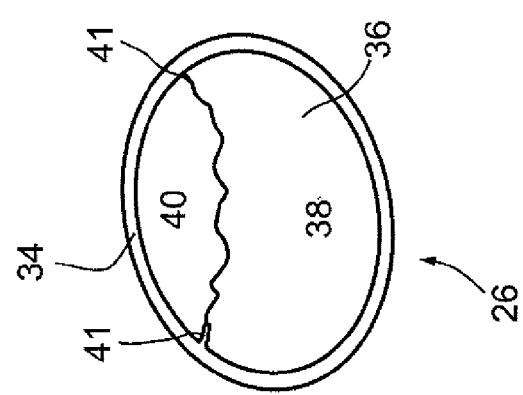

In an embodiment of the present invention, an anterior leaflet 38 is augmented, for treating a subject suffering from hypertrophic obstructive cardiomyopathy. The augmentation of anterior leaflet 38 moves coaptation depth 42 out of the systolic outflow. In addition, the stiffening of anterior leaflet 38 by deployment of an obstructor such as obstructor 94 therein leads to a posterior shift of chordae 46 (FIG. 2B) attached to leaflet 38, stretching chordae 46 and enhancing coaptation of leaflets 38 and 40.

Exemplary Multiple Cuts Embodiments

As noted above, in some embodiments a plurality of holes are made in the mitral valve leaflet. A plurality of holes may be advantageous over a single hole in several aspects, for instance, multiplicity of holes may be formed in a manner that makes better usage of the available space of the mitral valve leaflet.

Forming several small holes may have similar effect to having one larger hole, but may be easier in practice. Dilating each of the smaller holes requires less force than dilating one large hole, and thus, dilating several small holes may be carried out more quickly than making one large hole.

In some embodiments, a plurality of holes is formed so as to facilitate conforming of the cuts to the shape of the leaflet, for instance, the plurality of holes may form an envelope going in parallel to the coaptation area. It is much more difficult to form a single hole having an edge parallel to the coaptation area, and even harder in a transcutaneous procedure.

In some embodiments of the invention, a plurality of holes is formed to enlarge the leaflet considerably without jeopardizing the chordae.

In some embodiments, the multiple holes are made small enough, such that blood flow through the small holes is much smaller than blood flow through a single larger hole having the same area as all the small holes together.

Figure 7A:
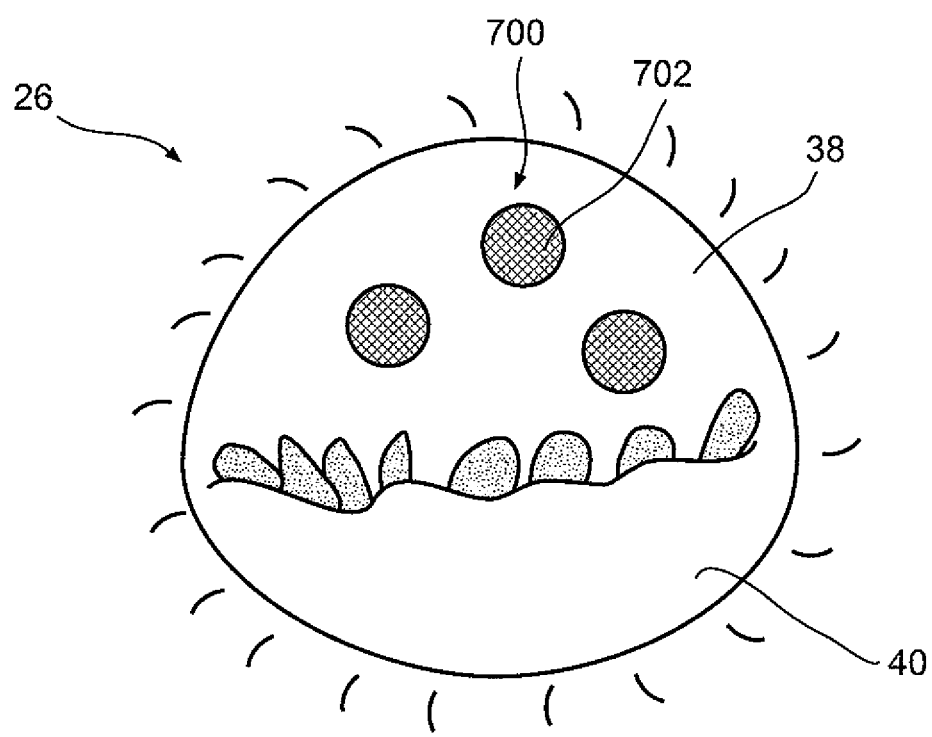
FIGS. 7A-7C are schematic illustrations of mitral valves having a plurality of obstructed holes according to an exemplary embodiment of the invention.

FIG. 7a is a schematic illustration of a mitral valve 26, having an augmented anterior leaflet 38. Leaflet 38 is augmented with three holes 700, obstructed with obstructors 702.

Figure 7B:
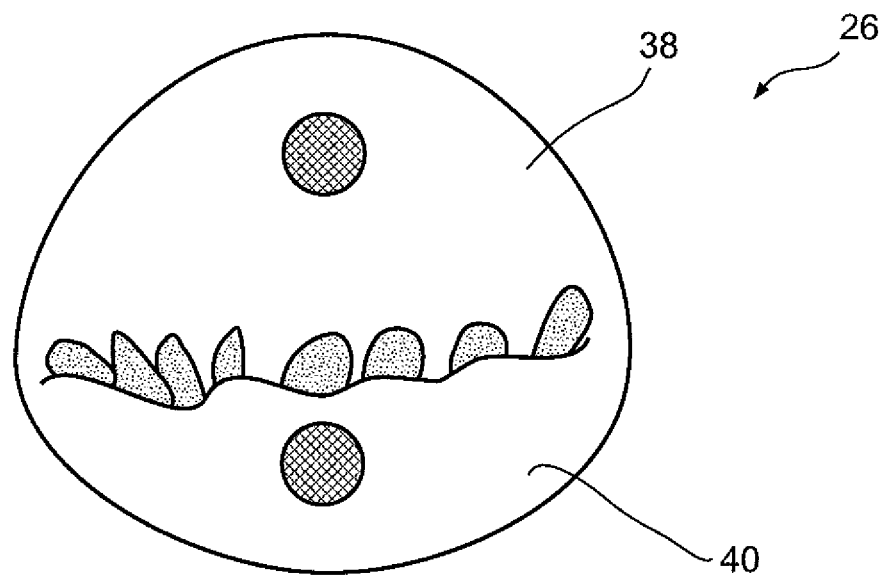

FIG. 7b is a schematic illustration of a mitral valve 26, having augmented anterior and posterior leaflets 38 and 40, each having one obstructed hole.

In some embodiments, augmenting both leaflets, rather than only one of them, is designed to cause each of the leaflets less distortion than would be caused to one of the leaflets if a larger cut is made in it. In some embodiments, coaptation improvement may be enhanced by augmenting both leaflets.

Figure 7C:
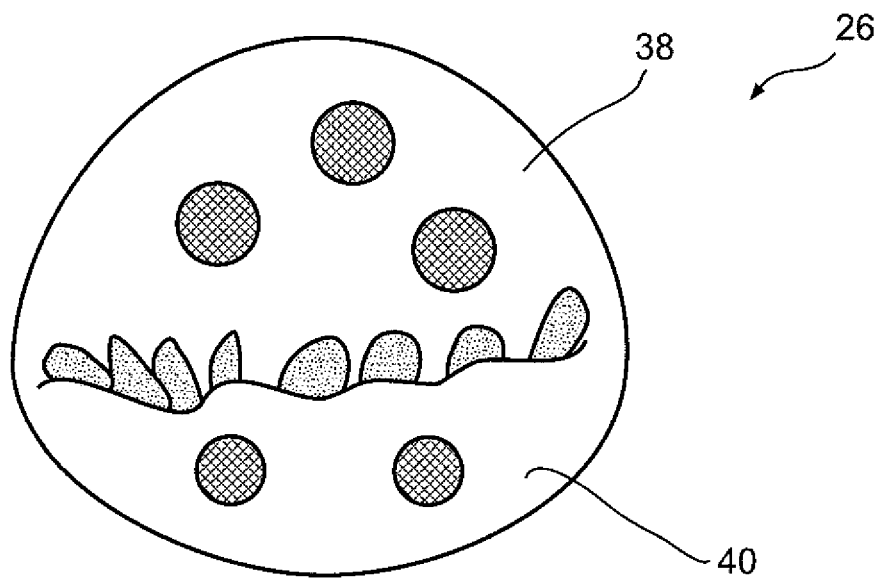

FIG. 7c is a schematic illustration of a mitral valve 26, having augmented anterior and posterior leaflets 38 and 40. Leaflet 38 is augmented with three obstructed holes and leaflet 40 with two.

In some embodiments, lots of holes are formed, for instance between about 5 and about 100, for example: 10, 20, 30, or 50 holes. Optionally, the holes are left unobstructed, and are naturally filled with tissue and/or blood coagulation. Optionally, many of the holes are obstructed with one obstructor.

FIG. 8 is a schematic illustration of a mitral valve 26 having a large number of small holes 800. Optionally, each of the holes is longitudinal, having a length of about 2-4 mm. Optionally, each of the holes is substantially parallel to commissures 41. Having the holes lie in parallel to commissures 41 helps in keeping the holes open by the natural stretching of the leaflet towards the commissures. More generally, blood pressure, annulus, and chordae all act to stretch the leaflets. Optionally, the size and/or shape of the holes is determined as to use these natural stretching forces to dilate the holes without using a dilation member.

Optionally, the holes (or some of them) are naturally obstructed by blood coagulation that occurs naturally at the holes.

In some embodiments, plurality 800 of holes is obstructed with a single obstructor, for example, of the kind depicted in FIG. 5c, going through one of the holes. Optionally, the final look of the mitral valve after a plurality of holes is obstructed with a single obstructor is similar to that shown in FIG. 4J.

In some embodiments, the mitral valve is allowed to stretch not by forming in it holes, but rather by cutting it to a portion of its thickness, thus reducing the leaflet's resistance to the stretching forces applied by the blood pressure, the chordae, and the annulus. Reducing the leaflet resistance to these natural stretching forces extends the leaflet to improve coaptation without forming holes in the leaflet, omitting the need to dilate or obstruct any hole.

A piercing element configured for forming such partial cuts is discussed below in the context of FIG. 11C.

FIG. 9 schematically illustrates one way of making a plurality of holes in a mitral valve arterial leaflet according to an embodiment of the invention. The figure shows piercing element 58 piercing an anterior leaflet 38 of a mitral valve 26 of an optionally beating heart.

When the heart beats the leaflet can move quite vigorously, making it very difficult to cut two holes in the leaflet at adjacent places as required, for instance, to form a plurality of holes as illustrated in FIG. 8.

Frame 900 is attached to leaflet 38. If the body of frame 900 is flexible enough, the frame repeatedly gets back to the same position at some points along cardiac cycles. If the body of frame 900 is less flexible, the frame remains in place; and only portions of the leaflet around the frame move when the heart beats. Optionally, in both cases the frame provides a reference frame that is fixed in relation to the catheter, allowing the surgeon better orientation in the leaflet after the leaflet flips during a heart beating.

Frame 900, also referred herein as a valve holder, optionally holds the leaflet to prevent the leaflet from retarding from the piercing element or from the knife, and to allow the surgeon to pierce the leaflet in adjacent places in an ordered manner.

Optionally, frame 900 is also useful in blocking blood from flowing through holes made in the leaflet. In some embodiments of the invention, the frame is retained attached to the leaflet after all necessary holes are formed, for example, to a period of about 10-15 minutes. This may be advantageous in that the frame prevents blood from washing through the newly-made holes, and thus, facilitates thrombi formation and/or growing of fibrous tissue to repair the tissue at the holes and retain the leaflet extended.

Frame 900 optionally comprises a conical tube with double walls 905 and 910. The area of the base of the cone is optionally 2.5-3 cm$^2$. The lumen defined between walls 905 and 910 is connected to a suction source (not shown), and the suction attaches frame 900 to leaflet 38. Optionally, frame 900 is also useful as a temporary obstructor, as it blocks blood from flowing from a cut inside the frame.

In some embodiments, each of walls 905 and 910 is reinforced with longitudinal wires (914, FIG. 9b) preventing the walls from collapsing to each other when vacuum is applied between the walls.

In some embodiments, Nitinol frame 900 is reinforced with springs 915 (FIG. 9c) provided between walls 905 and 910 to prevent the walls from collapsing to each other when vacuum is applied between the walls.

In some embodiments, frame 900 also comprises a mesh 920. Mesh 920 is useful in directing piercing element 58 to cut the leaflet only in the mesh openings, thus facilitating creating an ordered plurality of holes of the kind depicted in FIG. 8. Optionally, mesh 920 is integral with frame 900. Optionally, mesh 920 and frame 900 are separate elements. Optionally, frame 900 and mesh 920 are delivered to the leaflet in separate lumens of the delivery catheter. Optionally, mesh 920 is made of super-elastic wires, allowing its self expansion upon releasing from the catheter.

Figure 10:
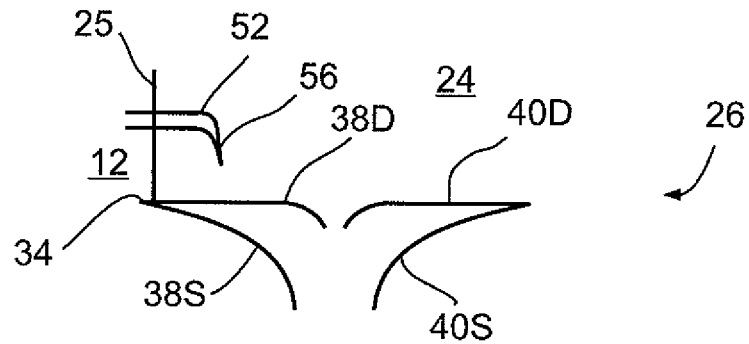
FIG. 10 is a schematic illustration of a mitral valve of a beating heart when cut according to an exemplary embodiment of the invention.

FIG. 10 is a schematic illustration of a mitral valve 26 of a beating heart when cut according to another exemplary embodiment of the invention. The figure schematically shows valve 26 at two states: at diastole (38D and 40D), and at systole (38S and 40S). As before, the numerals 38 and 40 refer to the anterior and posterior leaflets, respectively.

A catheter 52 with a piercing element 58 is shown going from right atrium 12 to the left atrium 24 through the interatrial septum 25, standing at the plain of annulus 34. In systole, anterior leaflet 38 is distanced from piercing element 58. In diastole, leaflet 38 moves and hits piercing element 58, thus impaling itself on element 58 and forming a puncture therein. In subsequent systole, leaflet 38 is retracted from the piercing element. Optionally, this systole period is used for moving piercing element 58 within the annulus plane, such that at next diastole, leaflet 38 will puncture itself at a different place. Piercing element 58 optionally has a small cutting tip, suitable for making cuts that do not form significant mitral insufficiency even if not obstructed.

Optionally, this process is carried out with the guide-wire withdrawn. Optionally, the process is carried out with a guide wire (not shown) going from the left atria through the leaflet, into the valve orifice. In such an option, if there is a need for urgent deployment of an obstructor to obstruct one or more of the holes formed in the procedure, an obstructor can be delivered quickly to the site using the guide wire. The guide wire is already in place, ready for guiding the obstructor.

Optionally, the process is carried out under imaging, such as ultrasonic doppler imaging, to allow the surgeon to decide when obstruction is required.

Optionally, after each cut is formed, the piercing element 58 is retracted, and the surgeon watches the image to estimate the results of the operation already carried out on the leaflet sufficiency and decide if further cuts and/or obstruction is required.

An Exemplary Piercing Element

In some embodiments of the invention, prior art piercing elements may be used. In some embodiments of the invention, a catheter delivered knife is used as a piercing element.

Figures 11A, 11B:
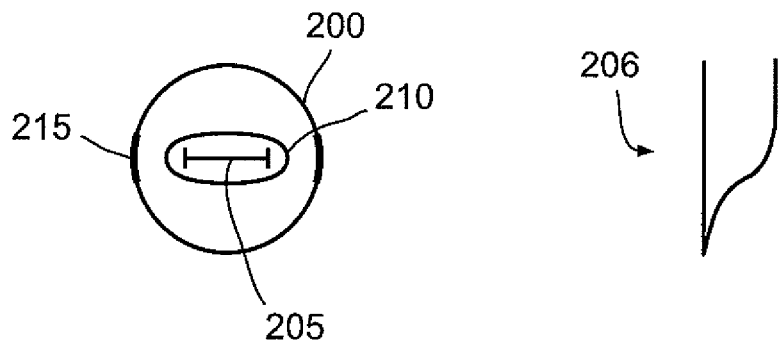
FIG. 11A is a schematic illustration of a cross section in a catheter delivering a knife according to an embodiment of the present invention.
FIG. 11B is a schematic illustration of a cross-section of a distal tip of a knife according to an exemplary embodiment of the invention.

FIG. 11a is a schematic illustration of a cross section in a catheter 200 delivering a knife 205 according to an embodiment of the present invention. Knife 205 is optionally delivered in a tube 210 defining within catheter 200 a lumen for knife 205.

Optionally, the cross-section of tube 210 is oval, allowing accommodation of a knife 205 configured for making elongated cuts.

Optionally, oval tube 210 has radio-opaque markers 215 at one or more sites along a longitudinal axis of the oval cross-section of tube 210, optionally near the distal end of the catheter. Such markers may be useful in indicating to the surgeon the orientation of knife 205 in relation to radio-imaged tissue in the vicinity of knife 205. Other orientation indicators may replace or join markers 215, as well known in the art of indicating orientation of catheters in relation to adjacent tissue.

Optionally, a cross-section of the cutting tip of knife 205 has an H-shape, as shown in the drawing, with sides that limit the movement of the knife inside a cut the knife makes in tissue.

FIG. 11B is a schematic illustration of a cross-section of a distal tip 206 of knife 205 in an exemplary embodiment. Distal tip 206 is configured for creating elongated cuts in tissue.

Figure 11C:
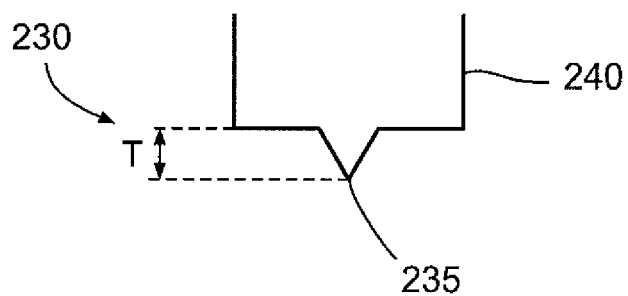
FIG. 11C is a schematic illustration of a cross-section of a distal tip 230 of a cutting element that provides cuts of limited thickness according to an exemplary embodiment of the invention.

FIG. 11C is a schematic illustration of a cross-section of a distal tip 230 of a cutting element that provides cuts of limited thickness according to an exemplary embodiment of the invention. Distal tip 230 has a cutting tip 235 and a stopper 240, for stopping cutting tip 235 from cutting a tissue deeper than to a depth T. Optionally, depth T is smaller than the thickness of a mitral valve leaflet, for example, about half the thickness of the leaflet. Since the thickness of arterior leaflet 38 is about 0.8-2.5 mm, in some embodiments of the invention distal tip is designed such that T is about 0.4-0.5 mm. Optionally, for cutting the posterior leaflet a knife with smaller cutting depth T is used, for instance cutting depth of 0.3-0.35 mm.

A piercing element with a distal tip 230 may be useful, for instance, in cutting the mitral valve leaflet only to a portion of its thickness, thus allowing the valve to stretch while leaving one of the leaflet's surfaces continuous, omitting the need to obstruct any hole.

In some embodiments, stopper 240 is used as a safety feature, preventing accidental puncturing of a heart tissue on the other side of the leaflet. Optionally, depth T is larger than the thickness of a mitral valve leaflet. Optionally, stopper 40 is comprised in a retractable tube, and the depth T may be controlled by the surgeon.

The present invention has been described herein primarily with reference to augmentation of the posterior mitral leaflet as embodiments of the present invention are useful in treating ischemic mitral regurgitation, a common pathological condition. It is understood, however, that embodiments of the teachings of the present invention are applied not to the posterior mitral leaflet but to the anterior mitral leaflet, or to leaflets of any other cardiac valve such as the tricuspid valve, the right atrioventricular valve or the left atrioventricular valve.

The present invention has been described herein primarily with reference to treatment of living human subjects, especially when the heart is beating. It is understood, however, that in embodiments the present invention is performed for the treatment of a non-human mammal, especially horses, cats, dogs, cows and pigs.

The present invention has been described herein primarily with reference to treatment of living subjects. It is understood that application of the present invention for training and educational purposes (as opposed to treating a condition) falls within the scope of the claims, whether on a living non-human subject or on a dead subject, whether on a human cadaver or on a non-human body, whether on an isolated cardiac valve, or on a valve in a heart isolated (at least partially) from a body, or on a body.

It is expected that during the life of this patent many relevant detectors, active entities and useful physical components such as pumps will be developed and the scope of the patent is intended to include all such a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of augmenting an atrioventricular valve leaflet, the method comprising:
    transcutaneously penetrating a leaflet of the valve to at least a portion of the leaflet's thickness to form a penetrated section; and
    extending said leaflet using said penetrated section, leaving the penetrated leaflet permanently obstructed so as to prevent blood flow through the penetrated section.

2. A method according to claim 1, wherein said atrioventricular valve is a mitral valve.

3. A method of according to claim 1, comprising:
    delivering, with a catheter, a penetrating element to the vicinity of the valve leaflet; and
    cutting, with said penetrating element, a valve leaflet to at least a portion of the leaflet's thickness so as to allow the leaflet to stretch.

4. A method according to claim 1, wherein penetrating a leaflet to at least a portion of the leaflet's thickness substantially consists of cutting to a portion of the leaflet's thickness so as to leave one of the leaflet's surfaces intact.

5. A method according to claim 1, wherein penetrating a leaflet to at least a portion of the leaflet's thickness comprises piercing the leaflet through the entire leaflet's thickness so as to form an opening going through the leaflet from one surface to the other.

6. A method according to claim 5, comprising dilating the opening.

7. A method according to claim 6, comprising: deploying a dilation brace in the dilated opening so as to maintain the dilated opening in a dilated state.

8. The method of claim 7, wherein said dilation brace includes an inflatable balloon.

9. The method of claim 8, wherein said dilation brace includes an expandable ring mounted on said inflatable balloon during said dilating.

10. The method of claim 7, wherein said dilation brace includes an expandable ring.

11. The method of claim 7, further comprising deploying a mitral valve annulus supporting device.

12. A method according to claim 1, wherein penetrating comprises performing a plurality of discontinuous penetrated segments.

13. A method according to claim 12, comprising: obstructing a plurality of said discontinuous penetrated segments with a single obstructor.

14. A method according to claim 1, comprising attaching to a surface of an atrioventricular valve leaflet a frame that holds a portion of the leaflet when the heart beats.

15. A method according to claim 14, wherein attaching comprises attaching by suction.

16. A method according to claim 14, wherein said frame comprises double walls from between which suction is applied, and the frame is configured to prevent collapsing of the walls towards each other when said suction is applied.

17. A method according to claim 14, wherein said penetration is guided by a guiding element.

18. The method according to claim 17, further comprising overlaying said guiding element on a portion of the leaflet, said penetrating comprising penetrating with the guidance of said guiding element, wherein said guiding element is integral with said frame.

19. A method according to claim 1, comprising overlaying a cutting guide on a portion of the leaflet, said penetrating comprising penetrating with the guidance of said cutting guide.

20. A method according to claim 19, wherein the cutting guide comprises a plurality of openings, and said penetrating comprises penetrating through a plurality of said openings.

21. A method of augmenting an atrioventricular valve leaflet, the method comprising:
    transcutaneously penetrating a leaflet of the valve to at least a portion of the leaflet's thickness to form a penetrated section,
    wherein said penetrating comprises:
    delivering a penetrating device to a first position in the vicinity of the leaflet during a first systole, such that at a first diastole the leaflet hits against the penetrating device and is penetrated at a first place.

22. A method according to claim 21, further comprising moving the penetrating device to a second position, such that at a second diastole the leaflet hits against the penetrating device and is penetrated at a second place.

* * * * *